(12) United States Patent
Wang et al.

(10) Patent No.: US 12,259,374 B2
(45) Date of Patent: Mar. 25, 2025

(54) METHOD FOR MULTI-INFORMATION FUSION OF GAS SENSITIVITY AND CHROMATOGRAPHY AND ON-SITE DETECTION AND ANALYSIS OF FLAVOR SUBSTANCES BASED ON ELECTRONIC NOSE INSTRUMENT

(71) Applicant: East China University of Science and Technology, Shanghai (CN)

(72) Inventors: Zejian Wang, Shanghai (CN); Daqi Gao, Shanghai (CN); Bo Li, Shanghai (CN); Xiaoqin Zhang, Shanghai (CN); Fang Cai, Shanghai (CN); Jianhua Li, Shanghai (CN); Mingjian Cheng, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 506 days.

(21) Appl. No.: 17/794,801

(22) PCT Filed: Jul. 18, 2020

(86) PCT No.: PCT/CN2020/102886
§ 371 (c)(1),
(2) Date: Jan. 25, 2023

(87) PCT Pub. No.: WO2021/147275
PCT Pub. Date: Jul. 29, 2021

(65) Prior Publication Data
US 2023/0141978 A1     May 11, 2023

(30) Foreign Application Priority Data
Jan. 23, 2020   (CN) .......................... 202010077153.1

(51) Int. Cl.
*G01N 30/88*   (2006.01)
*G01N 33/00*   (2006.01)
*G06N 3/045*   (2023.01)

(52) U.S. Cl.
CPC ......... *G01N 30/88* (2013.01); *G01N 33/0032* (2013.01); *G01N 33/0034* (2013.01);
(Continued)

(58) Field of Classification Search
CPC ............... G01N 30/88; G01N 33/0032; G01N 33/0034; G01N 33/0062; G01N 2030/8804; G01N 2030/8809; G06N 3/045
(Continued)

(56) References Cited

U.S. PATENT DOCUMENTS

2002/0182739 A1*  12/2002  Sadik ................. G01N 33/0031
                                                                  422/89
2016/0161459 A1*   6/2016  Rouse ...................... G01N 1/28
                                                                  73/31.07

(Continued)

FOREIGN PATENT DOCUMENTS

CN          1453584 A   *  11/2003
CN          1194227 C   *   3/2005
(Continued)

OTHER PUBLICATIONS

Zhang et al., A miniaturized electronic nose with artificial neural network for anti-interference detection of mixed indoor hazardous gases, Sensors & Actuators: B. Chemical 326 (2021) 128822 (Year: 2021).*

(Continued)

*Primary Examiner* — Stephanie E Bloss
*Assistant Examiner* — Kevin C Butler
(74) *Attorney, Agent, or Firm* — Taft Stettinius & Hollister LLP

(57) ABSTRACT

Provided is a method for multi-information fusion of gas sensitivity and chromatography and on-site detection and analysis of flavor substances using an electronic nose instrument. The electronic nose instrument includes a gas sensor array module (I), a capillary gas chromatographic column module (II), an automatic headspace sampling module (III), a computer control and data analysis module (IV), an automatic lifter (V) for headspace sampling, a large-volume headspace vapor generation device (VI) and two auxiliary gas sources (VII-1, VII-2). In the gas sampling period of (Continued)

T0-300-600 s, the gas sensor array module and the gas chromatography module have different flow rates, volumes and staring sampling time points of gas sampling, but have synchronous selection and analysis time points of multiple sensitive information. The electronic nose instrument obtains a 69-dimensional combined pattern, including steady-state response peak values, corresponding peak time points as well as under-curve areas, through each on-site real-time detection to a tested sample. The electronic nose instrument detects a large number of odorous samples to establish a big odor data. On this basis, the normalization fusion preprocessing is done, and the cascade machine learning model realizes both an on-site recognition of many foods, condiments, fragrances and flavors, and petroleum waxes and a real-time quantitative prediction of their odor quality grades and many key component concentrations.

10 Claims, 9 Drawing Sheets

(52) U.S. Cl.
CPC ......... *G01N 33/0062* (2013.01); *G06N 3/045* (2023.01); *G01N 2030/8804* (2013.01); *G01N 2030/8809* (2013.01)

(58) Field of Classification Search
USPC ....................................................... 73/31.07
See application file for complete search history.

(56) References Cited

U.S. PATENT DOCUMENTS

2023/0141978 A1\* 5/2023 Wang ..................... G06N 3/045
73/31.07
2023/0152287 A1\* 5/2023 Wang ..................... G06N 3/084
73/23.34

FOREIGN PATENT DOCUMENTS

| | | | | | |
|---|---|---|---|---|---|
| CN | 101858854 | A | \* | 10/2010 | |
| CN | 103439397 | A | \* | 12/2013 | |
| CN | 107843695 | A | \* | 3/2018 | ......... G01N 33/0001 |
| CN | 109655532 | A | \* | 4/2019 | |
| CN | 110018203 | A | \* | 7/2019 | ........... G01N 27/125 |
| CN | 111443161 | A | \* | 7/2020 | ............. G01N 30/88 |
| EP | 1376122 | A1 | \* | 1/2004 | ............. G01N 30/40 |
| WO | WO-2015009613 | A2 | \* | 1/2015 | ............... G01N 1/28 |

OTHER PUBLICATIONS

Wojnowski et al., Electronic Noses in Medical Diagnostics, Current Medicinal Chemistry, 2019, 26, 197-215 (Year: 2019).\*
El Barbari et al, Building of a metal oxide gas sensor-based electronic nose to assess the freshness of sardines under cold storage, Sensors and Actuators B 128 (2007) (Year: 2007).\*
Goschnick et al., Water pollution recognition with the electronic nose KAMINA, Sensors and Actuators B 106 (2005) 182-186 (Year: 2005).\*
First Office Action; The State Intellectual Property Office of People's Republic of China; Patent Application No. 202010077153.1; Sep. 27, 2020; 9 pages total.
International Search Report; China National Intellectual Property Administration; Patent Application No. PCT/CN2020/102886; Oct. 29, 2020; 4 pages.
Written Opinion; China National Intellectual Property Administration; Patent Application No. PCT/CN2020/102886; Oct. 21, 2020; 4 pages.

\* cited by examiner (a), Less than 10 chromatographic peaks within the specified interval (b), More than 10 chromatographic peaks within the specified interval (a), Response curve of gas sensor TGS826 to headspace vapor of petroleum wax sample A (b), Response curve of gas sensor TGS832 to 2,000ppm ethylene vapor (c), Response Curve of gas sensor TGS822 to 5,000ppm ethanol vapor (a), Learning process (b) Decision-making process

METHOD FOR MULTI-INFORMATION FUSION OF GAS SENSITIVITY AND CHROMATOGRAPHY AND ON-SITE DETECTION AND ANALYSIS OF FLAVOR SUBSTANCES BASED ON ELECTRONIC NOSE INSTRUMENT

CROSS REFERENCE TO RELATED APPLICATION

This is a U.S. national stage application filed under 37 U.S.C. 371 based on International Patent Application No. PCT/CN2020/102886, filed on Jul. 18, 2020, which claims priority to Chinese Patent Application No. 202010077153.1, filed with the China National Intellectual Property Administration (CNIPA) on Jan. 23, 2020, the disclosures of which are incorporated herein by reference in their entirety.

TECHNICAL FIELD

The present disclosure provides a method for multi-information fusion of gas sensitivity and chromatography and on-site detection and analysis of flavor substances using an electronic nose instrument, which is oriented to the disposable on-site real-time detection and analysis demand of the representative odorous (aromatic) substances including foods, condiments, fragrances and flavors, and petroleum waxes, deals with artificial intelligence, computer, analytical chemistry and other technical fields, and mainly solves such problems as unsatisfactory sensitivity and selectivity of conventional electronic nose instruments, poor real-time capability of chromatography, optimal structure combination of functional gas sensitive and gas chromatographic modules, multi-information selection and fusion of gas sensitivity and gas chromatography, and on-site real-time detection and analysis of electronic nose instruments.

BACKGROUND

Odor is invisible and intangible, a complex sense of biological olfactory, and a mixture of dozens, hundreds or even thousands of volatile components. Olfactory is a complex sensation of a large number of olfactory cells in a biological nasal cavity, and is the most mysterious among all senses. The working principle of biological olfactory systems had been clarified creatively by Axel and Buck, winners of 2004 Nobel Prizes in Physiology or Medicine: about 1,000 different receptor genes crossly perceive odors to form a large number of patterns (samples), and thus the brain can memorize and recognize tens of thousands of odors samples [1-2]. The bio-olfactory systems give inspiration and enlightenment to artificial olfactory system, namely electronic nose theory and application research, and its working principle has been always imitated.

Up to now, the relationship between odors' compositions and their types and intensities is still quite unclear, and the terms to descript this kind of relationship are both abstract and poor. The present status of odor (smell) quality evaluation for flavor substances is: either no standard exists or the current standards only depend upon the sensation of people, which leads to the related evaluation indices to exist in name only. Both the current Chinese National Standard GB/T1535-2017 about edible vegetable oils and the current Chinese Industrial Standard SH/T0414-2004 about petroleum waxes, for example, contain the odor (smell) quality indices, but the designated evaluation methods entirely depend upon the olfactory of people. The sensory sniffing methods for determining multiple quality index values of odors/smells have always been criticized not only for their complicated evaluation process, poor objectivity and fairness, low efficiency, high cost, poor operability, but also for their serious damage to the body by long-time smelling some seemingly harmless odors, which is quite against the desire of people for pursuing better life and the new era of artificial intelligence.

According to the olfactory simulation or electronic nose method, multiple gas sensitive elements with overlapped performances are used for forming an array to realize a rapid detection of odors (smells), and the qualitative and quantitative analysis of the odors is performed by using a machine learning method. The current state of the theoretical research on electronic nose is that the sensitivity of the gas sensors has reached $10^{-7}$ (VN), namely 0.1 ppm order of magnitude, but their selectivity is poor. Therefore, the stability, online characteristic and qualitative and quantitative capabilities of the electronic nose instrument are poor. The electronic nose instrument has attracted much attention due to its fast sensitive speed, non-contact detection, simple and convenient operation and the others, and the related on-site odor (smell) detection and analysis techniques have become a core application in food and other industries. At present, the domestic electronic nose application market is basically monopolized by France, Germany and other foreign products. Under the background of great demand, the electronic nose technology and application are listed in the national high technology R&D program (863), the national science and technology support program and the national key R&D program by the Ministry of Science and Technology of China many times.

The electronic nose instrument mainly adopts a one-off real-time on-site detection and analysis manner to identify, quantitatively estimate and predict the odors (smells) of foods, condiments, fragrances and flavors, petroleum waxes, cigarettes and others, and the qualitative and quantitative analysis is performed by means of one-time sensitivity of headspace vapor of a single tested sample. At the moment, the single detection period, for example, 5 min-10 min, the early-stage sample preparation process as well as the headspace vapor sucking flow, duration and accumulated volume are fixed, but the sample detection site and detection interval are not fixed, the headspace vapor volume is limited, the detection may be done at any time or site, and thus the headspace vapor generation and thermostatic device and the automatic sampling device need to be configured.

One of the main development trends of the electronic nose technology is to use an array of multiple gas sensor elements with necessary overlapped sensitivity, to improve the qualitative and quantitative capabilities of complex odors (smells) in combination with big data and artificial intelligence technologies, finally realize the identification of various odor types and quantitative prediction of intensity and key components. The basic premise of the electronic nose instrument for realizing a "real-time on-site" detection and analysis working manner is that the electronic nose instrument has a remarkably sensitive capability on the tested odors. From the application point of view, performance indices that the gas sensors should reach include an enough high sensitivity (ppm level or above), an enough fast response speed (within 1 min), a stable working state, high commercialization degree, a long service life (3-5 years), a small size, and a good selectivity.

Ref [3] lists the sensory properties of 6 typical gas sensitive elements: metal oxide semi-conductor (MOS), electrochemical (EC), conductive polymer (CP), quartz microbalance (QMB), surface acoustic wave (SAW) and photo ionization detector (PID) according to the difference of sensitive materials and working principles. Table 1 compares the characteristics of the 6 gas sensitive types and a gas chromatography (GC). Compared with the MOS type, an EC-type gas sensor has better selectivity, but much larger size, at least a year shorter life and lower than an order of magnitude sensitivity. Still compared with the MOS type, a PID-type gas sensor not only has large size, narrow sensitive range, high price and about half a year life. Moreover, the EC and PID gas sensors are more used for the detection of malodorous pollutants. The sensitivity of QMB and SAW gas sensors is one order of magnitude lower than that of MOS. Therefore, the sensitive membrane materials need to be further developed and the sizes need to be further reduced. The most suitable sensitive elements for the electronic nose instruments are the MOS-type gas sensors represented by $SnO_2$.

composable organic matters, but also difficult to qualify the unknown components, and therefore is not suitable for analyzing either the single compounds with strong polarity or complex compounds with large polarity difference or some compounds without carbon. For example, a gas chromatography using a hydrogen flame ionization detector (FID) cannot effectively detect some inorganic compounds.

Table 1 indicates that the gas chromatography is good while MOS gas sensors are poor in selectivity. It should be pointed out that this difference is relative and the "qualitative capability" of the gas chromatography to unknown samples is still "weak". If there is no a spectrogram database of internal/external standard samples, it is impossible to determine the components and constitution of an unknown sample at all only depending upon a piece of spectrogram obtained from one measurement. Another drawback is that the "selection capability" of a chromatographic column is not perfect. Only in specific cases, a specific chromato-

TABLE 1

Characteristics and comparison between 6 typical gas sensitive materials and a gas chromatographic column

| Type | Sensitivity | Selectivity | Response time | Stability | Size | Simplicity | Economy | Sensitive range | Lifespan/ year | Maintain ability | Auxiliary gas | Commercialized degree | Working condition |
|---|---|---|---|---|---|---|---|---|---|---|---|---|---|
| MOS | very high | poor | short | average | small | very good | very good | wide | 3~5 | not needed | not | high | on-site |
| EC | low | better | shorter | good | average | average | average | narrower | 1~2 | often | yes | average | on-site |
| CP | average | average | average | average | small | average | average | narrower | 1 | often | yes | low | on-site |
| QMB | low | poor | better | average | average | average | average | narrow | 1 | often | not | average | on-site |
| SAW | high | poor | short | good | average | average | average | narrower | 1 | often | not | low | on-site |
| PID | high | poor | short | poor | average | average | average | narrow | 5 | often | not | average | on-site |
| GC | very high | good | very long | very good | big | very poor | poor | very wide | 3~5 | often | yes | high | harsh |

A large number of experiments indicate that $S_nO_2$ semi-conducting gas sensor is fast in response to some odors, for example, only 2 s is needed for ethanol; whereas the response to other odors is slow, up to 30 s, 60 s or longer, for example, to sense the odor of petroleum waxes. This phenomenon tells us that although the steady state maximum values of response curves of a single gas sensor to two odors may be the same, the peak time points and the areas under two curves may be different; or the areas under the curves may be the same, but the steady state maximum values and peak time points may be different, and so on. In summary, the shape of the gas sensor response curve is related to the compositions of odors, which involves many factors such as a molecular weight, a carbon number, a polarity, a functional group.

The gas sensor has the advantages of being high in response speed, not strict in working condition requirement, poor in selectivity and not ideal enough in sensitivity. The 6 single-type gas sensitive elements and their arrays thereof are very limited in sensitive capability, and cannot meet the on-site detection requirements of foods, condiments, petroleum waxes and fragrances and flavors at any time. On the one hand, a large number of redundant gas sensitive elements to constitute an array will lead to a complex electronic nose instrument structure, but on the other hand, the overlapping sensitive range of the array is still limited[3]. The gas chromatography has therefore attracted great attention. The advantage of chromatography is good selectivity, and the Heracles II gas chromatography electronic nose commodity by aMOS Corporation, France, has emerged. In principle, the gas chromatography is not only difficult to analyze inorganic matters or high-boiling-point easily-degraphic column is sensitive to a specific sample, i.e. a specific chromatographic column can only detect a specific range of a specific sample. When either the sampling condition or the test condition or the chromatographic column parameter changes, and the chromatographic parameter for the specific sample will change. Many factors need to be considered for selecting a suitable chromatographic column, such as column material, stationary phase, inner diameter, film thickness, column length, tested samples, polarity.

The third drawback of the gas chromatography is that the more components in a tested object, and the closer the polarities between the components and thus correspondingly their retention time points, the more difficult to achieve "complete separation" of multiple peaks in a multi-component chromatogram at the cost of long detection time durations, and even impossible to do so in many cases. We believe that complete separation of multicomponent peaks in chromatograms is relative and rare; on the contrary, incomplete separation or semi-separation of the multicomponent peaks is absolute and universal, and complete separation is only an ideal or limiting case. It should be pointed out that the core of the gas chromatography is separation, not detection.

In order to improve a detection speed of the gas chromatography, a capillary column with a larger inner diameter of ϕ0.53 mm may be selected, the column length may be 30 m, and the sampling flow rate of the tested odor may be 1.0 ml/min-15 ml/min and the sampling time length may be 0.5 s-1.5 s within the gas sampling period T≤10 min. At this duration, a chromatogram with limited and some incompletely separated peaks is obtained, namely a semi-separated multi-peak chromatogram. A so-called "semi-separated" or "incompletely separated" chromatogram refers to such a chromatogram that is not completely separated between peaks in a specified time interval. The incompletely separated phenomenon is the result of the combined role of many factors, including the components of a tested odor, the characteristics of a chromatographic column, the setting of working parameters, the detector performance, and the time length of a recorder. A semi-separated chromatogram is a part of its full-separated correspondent. As long as the components and the test conditions remain unchanged, the semi-separated chromatogram obtained from for the same sample at different time points will remain unchanged, and their positional relationship with the full-separated chromatogram will also remain unchanged. It means that the semi-separated chromatogram may be used for inferring some of the main characteristics of the corresponding full-separated chromatogram, including the presence and content of some constituents with long retention time points.

Why should a gas sensor array and a capillary gas chromatographic column be combined? One of the reasons is that the gas sensors are still relatively poor both in selectivity and in sensitivity for some compounds, say some non-reducing/oxidizing inorganic compounds, due to the limitation of the current technical level. The second reason is that the gas chromatography is poor in online performance and a single chromatographic column is still limited in selectivity. For example, the gas chromatography is only able to detect the samples with good thermal stability. According to an incomplete statistics, the Agilent Technologies, Inc. provides thousands of ready-to-use chromatographic columns. A single chromatographic column is yet limited in detection range, which is clarified by such a fact that "a selected or replaced chromatographic column is only suitable for a specified sample". In terms of sensitive range, either a single chromatographic column or a single-type gas sensor array is limited, which is the reason why the online detection and analysis method of an electronic nose instrument fuse the gas sensor array and the capillary gas chromatographic column in the present disclosure. A response speed of a chromatographic column is at least one order of magnitude lower than that of the gas sensor, and an attempt to completely separate multiple peaks will further leads the chromatography not to meet the on-site odor detection requirement. In order to achieve a wide online sensitive range of odor compounds, the problem to be solved is how to combine the gas sensor array and the chromatographic column with complementary advantages to realize a on-site real-time detection with a period of about 10 min.

In order to realize the online detection and analysis method of an electronic nose instrument fusing the gas sensor array and the capillary gas chromatographic column, the following theory and technical problems for odor sensitivity and analysis must be solved:

(A) Multi-sense information selection and fusion of the gas sensor array and the gas chromatographic column is performed to realize an on-site rapid analysis.

The odor is characterized by: (1) numerous and complex constituents; (2) some chemical components have a low olfactory threshold, but have a large contribution to odor intensity, and vice versa. Some components contribute little to odor intensity, but the gas sensors are sensitive, and vice versa.

The triangular stability principle means that three sides (straight lines) are connected head to end to form a stable structure, which will not deform under force. A parallelogram is easily deformed under force and thus is unstable; similarly, polygons with more than three sides are all so. The triangle stability principle inspires us that it is impossible to determine a triangle structure if only two parameters (three cases in total, such as 2 side lengths, 2 included angles, and 1 side length plus 1 included angle) are known. Needless to say, it is not feasible to know only one parameter (two cases, namely 1 side length and 1 included angle). By means of inspiration, multiple pieces of feature information may be extracted simultaneously from the response curve of a single gas sensor to meet the triangular stability principle, for example, such three pieces of feature information as the "steady-state" response maximum value, the peak time value and the area under the curve are selected simultaneously, which is equivalent to improving the selectivity of the electronic nose instrument from the perspective of signal preprocessing.

In a marathon race that has already started for a certain time stage, although the champion or runner-up have not yet emerged, the winning or losing trend has become clear, and the first and second runners are in the "leading competition team ahead", that is a life prototype for online detection and analysis by using a semi-separated chromatogram. The early semi-separated chromatogram may be regarded as the "leading competition team ahead". For type identification and intensity and main component quantitative prediction of odors, the semi-separated chromatogram actually contains the main information of the full-separated correspondent, and the key is how to obtain the required information from the chromatogram and explain it. For practical purposes, the present disclosure proposes that several top peaks, the corresponding retention time points as well as the area under the whole curve are extracted from a semi-separated chromatogram in a specified time interval (say T=10 min or so) as the sensitive information features of the capillary chromatographic column to the tested object.

(B) Optimal combination of multiple functional modules including a gas sensor array, and integration and automation of an electronic nose instrument.

Since the odor constituents are numerous and the environment is changeable, it is uneconomical or even unrealistic to use redundant gas sensor elements to form an array to detect all odors. It has been pointed out that either a single chromatographic column or a single-type gas sensor array is limited in capability. Therefore, a method of optimization and fusion of a gas sensor array and a gas chromatographic column should be invented, namely, odor sensitivity, gas auto-sampling, a driving and control circuit, a computer and the like are functionally modularized and integrated in a test box, and a small-size, light-weight and easy-to-use electronic nose instrument is developed, the working status of each above-mentioned part is precisely controlled, the internal working condition of the instrument is optimized, in order to effectively cope with the external "changes" with the internal "constant" instrument.

(C) On-site analysis capability and intellectualization of the electronic nose instrument based on big data and machine learning.

Big data and artificial intelligence technologies have profoundly changed people's life and work ways. If there are such data as multi-source sensitization by a large number of on-site odor tests, sniffing a large number of odorous samples by professional panels, and component detection by conventional instruments including gas chromatography/mass spectrometry, it is impractical to attempt to estimate the intensity of complex odors and the concentrations of multiple constituents purely by means of a single-type gas sensor array, a single gas chromatographic column and a single machine learning model. Although many electronic nose instruments do so, the effect of the detection data is quite limited, and thus the results obtained are untrustworthy.

Due to the odor complexity and environmental variability, small dataset is not sufficient to train an effective machine learning model to identify the types of odors and quantitatively predict the concentrations of their complex constituents. Big odor data should be established on the basis of the detection data by the multi-source gas sensors/gas chromatography, the sniffing of panels, and the conventional gas chromatography/mass spectrometry. With the big data, a machine learning method can qualitatively identify the odor types and quantitatively predict their constituent concentrations through data mining according to the current sensitive information. Big data and real-time prediction of odor components are two contradictory aspects. An effective solution is that the machine learning model and algorithms which are as simple and effective as possible are invented to realize the type identification and the real-time quantitative prediction of intensity and multi-component concentrations of complex odors.

REFERENCES

[1] L. Buck, R. Axel, A novel multigene family may encode odorant receptors: A molecular basis for odor recognition, Cell, 1991, 65(1): 175-187.
[2] The Nobel Prize in Physiology or Medicine 2004 was awarded jointly to Richard Axel and Linda Buck, Available at: https://www.nobelprize.org/prizes/medicine/2004/summary, Oct. 4, 2004.
[3] P. Boeker, On 'Electronic Nose' methodology, Sensors & Actuators B—Chemical, 2014, 204: 2-17.

SUMMARY

The present disclosure is based on the existing invention patents: "a simulated olfactory instrument and a simultaneously qualitative and quantitative analysis method for various odors" (Chinese patent application No: 201010115026.2), "a simulated olfactory instrument and an on-site analysis method of odor grade for the specified substances" (Chinese patent application No. 20131031548.2), and provides a multi-information fusion method of an electronic nose instrument based on gas sensitivity and gas chromatography, and an on-site real-time detection and analysis method of flavor substances, to solve the identification of types, quantitative estimation and prediction problems of quality grades and main component concentrations for such flavor substances as foods, condiments, fragrances and flavors, and petroleum waxes.

In order to achieve the above objectives, the present disclosure provides the following technical schemes.

A method for multi-information fusion of gas sensitivity and chromatography and on-site detection and analysis of flavor substances using an electronic nose instrument is provided. The electronic nose instrument includes a gas sensor array module I, a capillary gas chromatographic column module II, an automatic headspace sampling module III, a computer control and data analysis module IV, an automatic lifter V for headspace sampling, a large-volume headspace vapor generation device VI, two auxiliary gas sources VII-1 and VII-2, which are configured to implement the real-time on-site detection and intelligent analysis of such flavor substances as foods, condiments, fragrances and flavors, and petroleum waxes.

The gas sensor array module I includes a gas sensor array I-1, an annular working chamber I-2 for installing the gas sensor array I-1, a thermal insulation layer I-3, a partition plate I-4, a fan I-5 and a resistance heating element I-6, and is located in the middle right part of the electronic nose instrument.

The capillary gas chromatographic column module II includes a capillary gas chromatographic column II-1, a detector II-2, an amplifier II-3, a recorder II-4, a thermal insulation layer II-5, a fan II-6, a resistance heating wire II-7 and an inlet port II-8, and is located in the right upper part of the electronic nose instrument.

The automatic headspace sampling module III includes a first two-position two-port electromagnetic valve III-4, a second two-position two-port electromagnetic valve III-5, a two-position three-port electromagnetic valve III-6, a second micro vacuum pump III-7, a third two-position two-port electromagnetic valve III-8, a fourth two-position two-port electromagnetic valve III-9, a side-hole sampling needle III-10, a first pressure relief valve III-11, a first purifier III-12, a second throttle valve III-13, a second pressure relief valve III-14, a second purifier III-15, a third throttle valve III-16, a second flowmeter III-17, a fourth throttle valve III-18 and a fifth throttle valve III-19, and is located in the right lower part of the electronic nose instrument.

Main constructional units of the computer control and data analysis module IV include an A/D data acquisition card IV-1, a driving and control circuit board IV-2, a computer mainboard IV-3, a 4-path precision DC stabilized power supply IV-4, a WIFI board card IV-5 and a display IV-6, and is located in the left side of the electronic nose instrument.

Main constructional units of the automatic lifter V for headspace sampling include a support disc V-1, a step motor V-2, a screw mechanism V-3 and a gear transmission mechanism V-4, and is located in a lower right front part of the electronic nose instrument. Main constructional units of the large-volume headspace vapor generation device VI include a thermal insulation layer VI-1, a resistance heating wire VI-2, a heat conduction sleeve VI-3, a temperature sensor VI-4, a tested sample VI-5, a 250 ml glass sample bottle VI-6, a silicone rubber sealing sheet VI-7 and a cup cover VI-8; one electronic nose instrument is provided with 4-6 large-volume headspace vapor generation devices VI.

The role of the large-volume headspace vapor generation device VI is to make 10 ml-30 ml tested sample at a constant temperature of 40-80±0.1° C. for about 30 min in the 250 ml glass sample bottle VI-6 at a test site, and thus generate 220 ml-240 ml headspace vapor. The role of the automatic lifter V is to make the large-volume headspace vapor generation device VI up 20 mm within 3 s, so that the side-hole sampling needle III-10 fixed under the inlet port of the annular working chamber I-2 penetrates through the silicone rubber sealing sheet VI-7 and contacts with the headspace vapor in the 250 ml glass sample bottle VI-6.

A gas sampling period of a headspace vapor by the electronic nose instrument for the tested sample VI-5 is T=300-600 s, and T=480 s by default. In a gas sampling period T, the sampling time length of a tested headspace vapor by the capillary gas chromatographic column module II is set to be earlier than that by the gas sensor array module I. In a case of T=480 s, the default headspace vapor sampling time point of the capillary gas chromatographic column module II is set to be 1 s earlier than that of the module I. The default sampling ratios of flow rates, durations and accumulated volumes for a tested odor by the gas sensor array module I to the capillary gas chromatographic column module II are set to be 1,000:6 ml/min, 60:1 s and 1,000:0.1 ml (theoretical value) in order. The computer control and data analysis module IV performs a sensitive information selection and analysis operation on the gas sensor array module I and the capillary gas chromatographic column module II at the same time.

In the gas sampling period T, the headspace vapor is sucked into the gas sensor array module I and the capillary gas chromatographic column module II by the first micro vacuum pump III-1 and the second micro vacuum pump III-7, respectively, so that the gas sensor array I-1 and the capillary gas chromatographic column II-1 can generate sensitive responses, respectively; the electronic nose instrument obtains 1 group of response curves of gas sensors and 1 gas chromatogram, i.e., an enlarged analog signals of gas sensitivity/gas chromatography, for sensing a tested odor sample by the electronic nose instrument.

In the gas sampling period T, the computer control and data analysis module IV extracts 48 response variables from multiple response curves of the gas sensor array module I and 21 feature variables from a limited-time-length semi-separated chromatogram of the capillary gas chromatographic column module II. Therefore, a 69-dimensional response vector $x(\tau) \in R^{69}$, or called a numerical pattern hereinafter, is obtained by the electronic nose instrument, which is saved in a corresponding data file of a hard disk in the computer mainboard IV-3; and then the numerical pattern $x(\tau)$ is sent to a cloud terminal and many specified fixed/mobile terminals through a WIFI routing module.

The electronic nose instrument goes through an on-site real-time detection over many months and years for many flavor substances, such as foods, condiments, fragrances and flavors, and petroleum waxes, and thus a big odor dataset X comes into being, a part of which have established the corresponding relationship between the numerical response patterns of gas sensor array/gas chromatography and the types, intensity grades and main component concentrations of the specified flavor substances.

In a learning stage, a cascade machine learning model of the computer control and data analysis module IV learns a normalized pre-processing big odor data X offline to determine the structure and parameters of the cascade machine learning model, and a recent gas-sensitive/gas-chromatographic response vector is learned online to finely tune the parameters of the machine learning model. In a decision-making stage, the cascade machine learning model determines types of various foods, condiments, fragrances and flavors, and petroleum waxes online according to a current gas-sensitive/gas-chromatographic response vector $x(\tau)$, and quantifies and predicts an odor intensity grade and the main component concentration values of an odor.

In the gas sampling period T, the headspace sampling moment of the capillary gas chromatographic column module II is performed earlier than that of the gas sensor array module I for a tested vapor. For example, when T=480 s, the headspace sampling moment of the capillary gas chromatographic column module II may be is earlier than that of the module I for the tested vapor. A sampling flow rate, a sampling duration and an accumulated sampling volume of the gas sensor array module I and the capillary gas chromatographic column module II are different for a tested odor, and the three default ratios are set to be 1,000:6 ml/min, 60:1 s and 1,000:0.1 ml in order. The computer control and data analysis module IV performs an information selection and analysis operation to the gas sensor array module I and the capillary gas chromatographic column module II simultaneously. The gas sensor array I-1 and the annular working chamber I-2 are located in a thermostatic working box with a temperature of 55±0.1° C.; in the gas sampling period T, the gas sensor array module I go through the following 6 stages in order: (i) a headspace sampling stage of the capillary gas chromatographic column module II for a tested odor, with a default duration of is and a default flow rate of 6 ml/min; (ii) a headspace sampling stage of the gas sensor array module I for a tested odor, with a duration of 60 s and a flow rate of 1,000 ml/min; (iii) a transitional stage with a duration of 4 s and a flow rate of 1,000 ml/min by the ambient air; (iv) a flushing stage with a duration of T−110 s by the ambient air, namely a rough recovery stage of the gas sensor array; (v) an accurate dry air calibration stage with a duration of 40 s; and (vi) a balance stage, i.e., a stage without gas flow, with a duration of 5 s. The "transitional stage" realize the conversion from the tested headspace vapor to the ambient air, and the ambient air is mainly used for as the rough recovery of the gas sensor array I-1, a flushing of the annular working chamber I-2 and the inner walls of related pipelines, and a removal of the accumulated heat volume generated by the gas sensor array.

A [1 s, 61 s] interval of in the gas sampling period T is the headspace sampling stage of the gas sensor array module I for a tested odor. In this stage, the second two-position two-port electromagnetic valve III-5 is set to be on, and the first two-position two-port electromagnetic valve III-4, the third two-position two-port electromagnetic valve III-8 and the fourth two-position two-port electromagnetic valve III-9 are set to be off. At the moment it does not matter whether the two-position three-port electromagnetic valve III-6 is on or off. Under a suction action of the first micro vacuum pump III-1, a headspace vapor of the tested sample VI-5 flows through, at a flow rate of 1,000 ml/min, the side-hole sampling needle III-10, the annular working chamber I-2 plus the gas sensor array I-1, the second two-position two-port electromagnetic valve III-5, the first throttle valve III-3 and the first flowmeter III-2 in order, and finally is discharged to outdoor lasting 60 s. During this stage, the gas sensor array 1-1 generates a sensitive response for the tested odor, and a response data is saved in a temporary file of the computer mainboard IV-3.

A [T−45 s, T−5 s] interval of the gas sampling period T is the dry air calibration stage of the gas sensor array module I. In this stage, the fourth two-position two-port electromagnetic valve III-9 is set to be on, the second two-position two-port electromagnetic valve III-5 is set to be off, and it does not matter whether the remaining electromagnetic valves are on or off. The dry air in the dry air bottle VII-2 flows through, at a flow rate of 1,000 ml/min, the first pressure relief valve III-11, the first purifier III-12, the second throttle valve III-13, the fourth two-position two-port electromagnetic valve III-9, the gas sensor array I-1 and the side-hole sampling needle III-10 inside the annular working chamber I-2 in order, and finally is discharged to outdoor for 40 s. During this period, the gas sensor array I-1 is accurately recovered to a reference state under the role of the dry air.

A [65 s, T−45 s] interval of the gas sampling period T is the flushing stage of the ambient air or the rough recovery stage of the gas sensor array. In this stage, the second two-position two-port electromagnetic valve III-5 and the first two-position two-port electromagnetic valve III-4 are set to be on, and the second two-position two-port electromagnetic valve III-9 is set to be off, whether the third two-position two-port electromagnetic valve III-8 and two-position three-port electromagnetic valve III-6 on or off is irrelevant. Under the suction action of the first micro vacuum pump III-1, the ambient air flows through, at a flow rate of 6,500 ml/min, the side-hole sampling needle III-10, the annular working chamber I-2 plus the gas sensor array I-1, the second two-position two-port electromagnetic valve III-5, the first two-position two-port electromagnetic valve III-4 and the first flowmeter III-2 in order, and finally the ambient air is discharged to outdoor for T−110 s. During this stage, the residual odor molecules on the inner walls of the related pipelines are washed away, the accumulated heat generated by the long-term work of the gas sensor array is taken away, and the gas sensor array I-1 is roughly recovered to a reference state under the role of the ambient air.

The commercially available capillary gas chromatographic column II-1 is length×inner diameter×film thickness=L×ϕd×δ=30 m×ϕ0.53 mm×0.25 μm in size, and is located in a thermostatic working box with a temperature of 250-300±0.1° C. In the gas sampling period T, the capillary gas chromatographic column module II goes through the following three stages: (i) a headspace sampling stage lasting is (default) for a tested odor; (ii) a gas chromatographic separation stage T−11 s (default); and (iii) a discharging, cleaning and purging stage by lasting 10 s. A duration of the headspace sampling stage for a tested odor is 0.5 s~1.0 s, the default duration is 1 s, and the range of sampling flow rate is 1.5 ml/min~15 ml/min with a default value of 6 ml/min. $H_2$ of the auxiliary gas source VII-1 is used as both a carrier gas and a fuel gas, and the dry air of the auxiliary gas source VII-2 is used as combustion-supporting gas.

An [0, 1 s] interval of the gas sampling period T is the headspace sampling stage of the capillary gas chromatographic column module II for the tested odor. In this stage, the two-position three-port electromagnetic valve III-6 is set to be at "1", the third two-position two-port electromagnetic valve III-8 is set to be on, and the second two-position two-port electromagnetic valve III-5 and the fourth two-position two-port electromagnetic valve III-9 are set to be off, whether the first two-position two-port electromagnetic valve III-4 is on or off is irrelevant. Under the suction action of the second micro vacuum pump III-7, the headspace vapor generated by the tested sample VI-5 flows through, at a flow rate of 1.5 ml/min-15 ml/min, the third two-position two-port electromagnetic valve III-8, the two-position three-port electromagnetic valve III-6 and the fourth throttle valve III-18 in order, then mixes with the carrier gas $H_2$ at the inlet port II-8, and thus flows into the capillary gas chromatographic column II-1 for 0.1 s-1.5 s. In a case of the sampling flow rate of 6 ml/min and the duration of 1 s, a cumulative sampling volume of the tested odor is 0.1 ml, which just meets an optimal sampling volume requirement of the capillary gas chromatographic column.

An interval of [1 s, T] in the gas sampling period T is the separating, discharging, cleaning and purging stage of the capillary gas chromatographic column module II lasting T−1 s. In this stage, the two-position three-port electromagnetic valve III-6 is set to be "2", and an on-off status of the other two-position two-port electromagnetic valves is irrelevant. Due to the pushing action of the carrier gas $H_2$, the tested odor is separated in the capillary gas chromatographic column II-1, and the detector II-2 thus generates a sensitive response. After amplified by the amplifier II-3, the sensitive response is record by the recorder II-4 in an interval of [0, 470 s] or a duration of 470 s, and then is saved in a temporary file of the computer mainboard IV-3. The response data is not recorded in the interval of [T−10 s, T] or the duration of 10 s in the discharging, cleaning and purging stage.

The gas sensor array module I and the capillary gas chromatographic column module II simultaneously enter an information selection and analysis region in the last 10 s of the gas sampling period T. The computer control and analysis module IV simultaneously selects the 3 pieces of sensitive information, namely, a steady-state maximum response $v_{gs\_i}(\tau)$, a corresponding peak time value $t_{gs\_i}(\tau)$ and an area $A_{gs\_i}(\tau)$, from a 60 s voltage response curve by the $i^{th}$ gas sensor in the [1 s, 61 s] headspace sampling stage of T, which is recorded in a temporary file, to meet the triangular stability principle and thus improve the qualitative and quantitative capability of the gas sensor array. The computer control and data analysis module IV obtains 16*3=48 sensitive variables in total from 16 response curves of the gas sensor array I-1 with 16 gas sensitive elements.

The computer control and data analysis module IV selects 21 sensitive variables from a semi-separated chromatogram by the capillary gas chromatographic column II-1 in an interval of [0, T−10 s] or a duration of T−10 s; where the 21 sensitive variables include the first 10 maximum peaks $h_{gc\_i}(\tau)$, the 10 corresponding retention time values $t_{gc\_i}(\tau)$, and an area $A_{gc}(\tau)$ under the chromatogram curve. If the number of the peaks in the semi-separated chromatogram with a duration of T−10 s is less than 10, say q<10, the computer control and data analysis module IV selects the first q<10 maximum peaks $h_{gc\_i}(\tau)$, the corresponding q<10 retention time points $t_{gci}(\tau)$, 1 area under the chromatogram curve, $A_{gc}(\tau)$, from the semi-separated chromatogram. and a zero-padded operation is performed for those Insufficient chromatographic peaks and retention time values; on which the chromatographic sensitive information obtained is $X_{gc}(\tau)=\{(h_{gc\_1}(\tau), h_{gc\_2}(\tau), \ldots, h_{gc\_q}(\tau), 0, \ldots, 0); (t_{gc\_1}(\tau), t_{gc2}(\tau), \ldots, t_{gc\_q}(\tau), 0, \ldots, 0); A_{gc}(\tau)\}$.

In the gas sampling period T, the computer control and data analysis module IV fuses 48 sensitive variables extracted from the 16 response curves of the gas sensor array I-1 and 21 sensitive variables extracted from the semi-separated chromatogram of the capillary gas chromatographic column II-1 through a normalized pre-processing to obtain a response vector $x(\tau) \in R^{69}$ with m=48+21=69 dimensions. The response vector $x(\tau) \in R^{69}$ is saved in a specified file of the hard disk of the computer mainboard IV-3, and then is used as a data basis of doing a qualitative and quantitative analysis on foods, condiments, fragrances and flavors, and petroleum waxes by the electronic nose instrument.

The computer control and data analysis module IV adopts a modular cascade neural network model to perform (i) identification and (ii) quantitative prediction of sensory qualitative index scores and main components for the foods, condiments, fragrances and flavors, and petroleum waxes. (i) The first level of the modular cascade neural network model includes n(n−1)/2 single-output neural networks to form n parallel vote recognition groups, and are used for identifying n foods, condiments, fragrances and flavors, and petroleum waxes, including brands, production places, authenticity and fragrance types, one for one. (ii) The second level of the modular cascade neural network model includes n×q single-output neural networks in parallel, in which every group has q single-output neural networks and are used for quantitatively predicting q indices, including the intensity grades and main component concentrations of n condiments, fragrances and flavors, and petroleum waxes.

In the first-level learning stage (i) of the modular cascade neural network model, the big odor data, namely the training set X, is executed the one-to-one task decomposition based on brands, production places, authenticity and types of odors to form n(n−1)/2 binary-class training subsets, and then the n(n−1)/2 training subsets are learned by n(n−1)/2 single-output neural networks in the first level of the modular cascade neural network model with the error back-propagation algorithm, one by one. The structures of all single-output neural networks are single-hidden-layer in structure, i.e., the number of input nodes is m=69, the number of hidden nodes is $s_1$=8, and the number of output nodes are 1. The n(n−1)/2 single-output neural networks form n vote recognition groups, and each single-output neural network only takes part in the voting two groups among.

In the learning stage of the second level (ii) of the modular cascade neural network model, the big odor data or the training set X is executed the one-to-one decomposition to form n×r single-output regression training subsets on behalf of brands, production places, authenticity and types of odors again. The n×q single-output neural networks in the second level of the modular cascade neural network model fit the multi-input single-output nonlinear relation curves of the q indices, one by one, in which are the relations between all the gas sensitive/gas chromatographic vectors $x_p$ and the intensity grades and the main component concentrations of the represented odors. All the single-output neural networks are single-hidden-layer in structure, i.e., the number of input nodes is m=69, the number of hidden nodes is $s_2$=5, and the number of output nodes is e1.

The modular cascade neural network model employs the majority voting decision-making rule to identify n kinds of foods, condiments, fragrances and flavors, and petroleum waxes. The decision-making rule for identifying the unknown pattern x is that x belongs to the brand, the production place, the authenticity and the type of the foods, condiments, fragrances and flavors, and petroleum waxes represented by the vote recognition group with the highest number of votes. On the premise that the vote number of the vote recognition group $\Omega_j$ is the highest in all the first-level groups, the quantitation prediction group $\Lambda_j$ in the second level groups corresponding to the first level vote recognition group $\Omega_j$ predicts the intensity level and main component concentration values of x.

The electronic nose instrument performs the on-site real-time detection and prediction of various foods, condiments, fragrances and flavors, and petroleum waxes, including the following steps:

(1) Power-on: the preheating time length of the electronic nose instrument is set to be 30 min; and the "gas sampling period T" in the screen menu is set to be a default value T=8 min.

The first two-position two-port electromagnetic valve III-4 and the second two-position two-port electromagnetic valve III-5 are set to be on, the fourth two-position two-port electromagnetic valve III-9 is set to be off, and the ambient air flows through, at the flow rate of 6,500 ml/min, the side-hole sampling needle III-10, the gas sensor array I-1 inside the annular working chamber I-2, the second two-position two-port electromagnetic valve III-5, the first two-position two-port electromagnetic valve III-4 and the first flowmeter III-2 in order, and finally is discharged to outdoor; and the internal temperature of the annular working chamber I-2 of the gas sensor array reaches a constant temperature of 55±0.1° C.

The two-position three-port electromagnetic valve III-6 is set to be at "2", under the pushing action of the carrier gas $H_2$, the capillary gas chromatographic column II-1 gradually recovers to a reference state, and the internal temperature in the chromatographic column box reaches a constant 250-300±0.1° C.

The preparation and constant temperature of a tested sample: an operator first pipets 10-30 ml tested sample VI-5 into the glass sample bottle VI-6, and then the glass sample bottle VI-6 is placed into the heat conduction sleeve VI-3 of the large-volume headspace vapor generation device VI, the silicone rubber sealing sheet VI-7 is covered, and the cup cover VI-8 is screwed. An confirmation key is pressed down to start the thermostat time, the tested sample VI-5 starts to be heated, the temperature rises to 45-80±0.1° C. from the room temperature within 8 min, and then accurately keeps the constant temperature for 20-30 min.

(2) Starting the gas sampling period T of the $k^{th}$ tested sample VI-5. Taking T=8 min as an example below.

(2.1) The gas sensor array module I:

(2.1a) The headspace sampling stage: in the 1 s-61 s interval of the gas sampling period T, the second two-position two-port electromagnetic valve III-5 is set to be on, the first two-position two-port electromagnetic valve III-4 and the third two-position two-port electromagnetic valve III-8 and the fourth two-position two-port electromagnetic valve III-9 are all set to be off. Under the suction action of the first micro vacuum pump III-1, the headspace vapor of the tested sample VI-5 flows through, at a theoretical flow rate of 1,000 ml/min, the side-hole sampling needle III-10, the annular working chamber I-2 and the gas sensor array I-1, the second two-position two-port electromagnetic valve III-5, the first throttle valve III-3 and the first flowmeter III-2 in order, and finally is discharged to outdoor for 60 s. Therefore, the gas sensor array I-1 generates a sensitive response for the tested odor, and the response data is saved in a temporary file of the computer mainboard IV-3 also for 60 s. The initial 0 s-1 s is the headspace sampling stage of the capillary gas chromatographic column II.

(2.1b) The transition stage: in the 61 s-65 s interval of the gas sampling period T, the second two-position two-port electromagnetic valve III-5 is set to be on, and the first two-position two-port electromagnetic valve III-4 and the third two-position two-port electromagnetic valve III-8 and the fourth two-position two-port electromagnetic valve III-9 are set to be off. The automatic lifter V makes the large-volume headspace vapor generation device VI go down by 20 mm within 3 s, and the first micro vacuum pump III-1 keeps sucking the tested odor at a flow rate of 1,000 ml/min accordingly. Along with the descending of the large-volume headspace vapor generation device VI, the gas flowing inside the annular working chamber I-2 for installing the gas sensor array I-1 is gradually transferred from the headspace vapor of the tested sample VI-5 to the ambient air.

(2.1c) The rough recovery stage: in the 65 s-435 s interval of the gas sampling period T, the first two-position two-port electromagnetic valve III-4 and the second two-position two-port electromagnetic valve III-5 are set to be on, the fourth two-position two-port electromagnetic valve III-9 are set to be off. Under the suction action of the first micro vacuum pump III-1, the ambient air flows through, at a flow rate of 6,500 ml/min, the side-hole sampling needle III-10, the gas sensor array I-1 inside the annular working chamber I-2, the second two-position two-port electromagnetic valve III-5, the first two-position two-port electromagnetic valve III-4 and the first flowmeter III-2 in order, and finally is discharged to outdoor for 370 s. Therefore, the gas sensor array I-1 roughly recovers to the reference state under the action of the ambient air.

(2.1d) The accurate calibration stage: In the 435 s-475 s interval of the gas sampling period T, the fourth two-position two-port electromagnetic valve III-9 is set to be on, the second two-position two-port electromagnetic valve III-5 is set to be off, and the dry air in the dry air bottle VII-2 flows through, at a flow rate of 1,000 ml/min, the first pressure relief valve III-11, the first purifier III-12, the second throttle valve III-13, the fourth two-position two-port electromagnetic valve III-9, the gas sensor array I-1 inside the annular working chamber I-2 and the side-hole sampling needle III-10 in order, and finally is discharged to indoor for 40 s. Therefore, the gas sensor array I-1 accurately recovers to the reference state. In the interval, an operator places the tested sample going through a precise thermostatic process with the large-volume headspace vapor generation device VI on the support disc V-1 of the automatic lifter V, and a preparation is done for the next headspace sampling period.

(2.1e) The balance stage: In the 475 s-480 s interval of the gas sampling period T, all the two-position two-port electromagnetic valves are set to be off, and no gas flows inside the annular working chamber I-2 for 5 s. From the 475$^{th}$ second, the automatic lifter V makes the large-volume headspace vapor generation device VI up 20 mm within 3 s.

(2.2) The capillary gas chromatographic column II module:

(2.2a) The headspace sampling stage: In the 0 s-1 s interval of the gas sampling period T, the two-position three-port electromagnetic valve III-6 is set to "1", the third two-position two-port electromagnetic valve III-8 is set to be on, and the second two-position two-port electromagnetic valve III-5 and the fourth two-position two-port electromagnetic valve III-9 are set to be off. Under the suction action of the second micro vacuum pump III-7, the headspace vapor of the tested sample VI-5 flows through, at a default flow rate of 6 ml/min, the third two-position two-port electromagnetic valve III-8, the two-position three-port electromagnetic valve III-6 and the fourth throttle valve III-18, mixes with the carrier gas $H_2$ at the inlet port II-8 in order, and then flows into the capillary gas chromatographic column II-1 for 1.0 s. In the stage the default accumulated sampling volume of the tested headspace vapor is 0.1 ml.

(2.2b) The gas chromatographic separation stage: In the [1 s, 480 s] interval of the gas sampling period T, the two-position three-port electromagnetic valve III-6 is set to be "2". Under the pushing action of the carrier gas $H_2$, the tested headspace vapor is separated in the 30 m capillary gas chromatographic column II-1 and thus the detector II-2 generates a sensitive response. with the help of the amplifier II-3, the recorder II-4 records the amplified sensitive response in the interval of [0, 470 s] or the duration of 470 s to form a semi-separated chromatographic peak graph, and then is saved in a temporary file of the computer mainboard IV-3.

(2.3) The information selection and analysis stage: In the 470 s-480 s interval of the gas sampling period T, the computer control and data analysis module IV selects 3 pieces of sensitive information, i.e., a steady-state peak value $v_{gs\_i}(\tau)$, a corresponding peak time value $t_{gs\_i}(\tau)$, and an area under the curve, $A_{gs\_i}(\tau)$, from the voltage response curve of each gas sensor which is recorded in the time stage of [1 s, 60 s]; and then select 21 sensitive response variables, i.e., the first 10 maximum chromatographic peaks $h_{gc\_j}(\tau)$, the corresponding 10 retention time values $t_{gc\_j}(\tau)$, and an area under the curve $A_{gc}(\tau)$ from the semi-separated chromatogram recorded in the time stage of [0 s, 470 s], which are saved in a temporary file of the computer mainboard IV-3. The computer control and data analysis module IV obtains one 69-dimensional response vector $x(\tau) \in R^{69}$ from the combined sensitive information of the gas sensor array module I and the capillary chromatographic column module II for the tested sample VI-5. Next the cascade machine learning model performs the identification of types and the quantitative prediction of whole intensity as well as concentrations of main components for a specified odor according to the response vector $x(\tau)$. The detection and prediction results are displayed by the monitor, and is transmitted to a central control room and multiple fixed/mobile terminals through the Internet.

(3) Repeat the step (2), and thus the electronic nose instrument realizes the on-site real-time detection, identification and quantitative prediction of intensity and concentration index values of many main components of foods, condiments, fragrances and flavors and petroleum waxes samples

DETAILED DESCRIPTION

The present disclosure will be further described in details by combining with the accompanying drawings.

Figure 1:
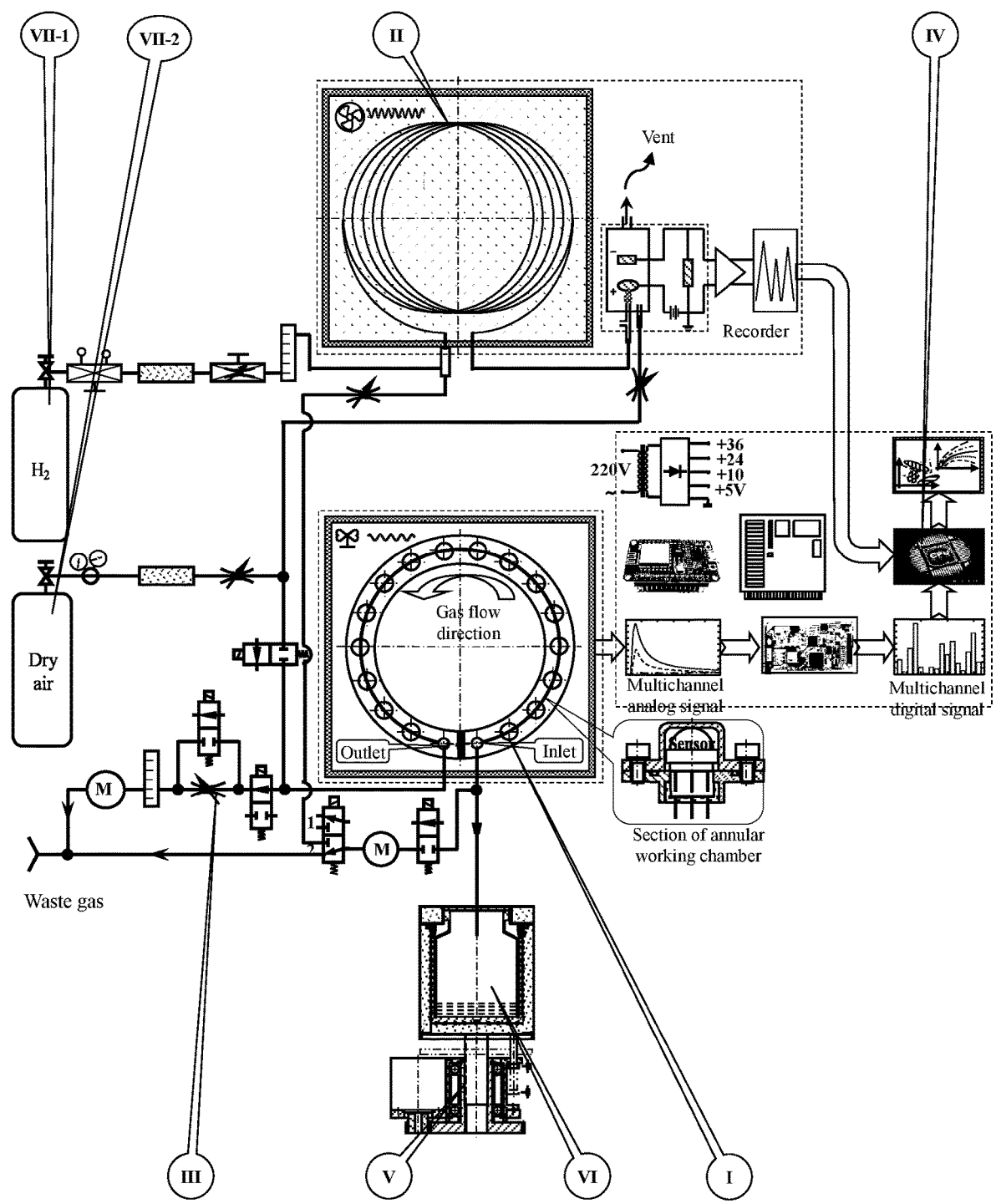
FIG. 1 is a schematic diagram of working principle of the electronic nose instrument, i.e., a schematic diagram of headspace sampling state of the gas sensor array module, in a method for multi-information fusion of gas sensitivity and chromatography and on-site detection and analysis of flavor substances using an electronic nose instrument provided in the present disclosure.

FIG. 1 is the schematic diagram of working principle of the electronic nose instrument in a method for multi-information fusion of gas sensitivity and chromatography and on-site detection and analysis of flavor substances using an electronic nose instrument provided in the present disclosure. Main constructional units of the electronic nose instrument include a gas sensor array module I, a capillary gas chromatographic column module II, an automatic headspace sampling module III, a computer control and data analysis module IV, an automatic lifter V, a large-volume headspace vapor generation device VI, a hydrogen bottle VII-1 and a dry air bottle VII-2. FIG. 1 shows a headspace sampling state of the gas sensor array module I. Hydrogen $H_2$ is used both as the carrier gas for the capillary gas chromatographic column module II and as the fuel gas for a Hydrogen flame ionization detector (FID). The dry air is used not only as the combustion-supporting gas of FID in the capillary chromatographic column module II, but also as the calibration gas (not combusted) in the gas sensor array module I.

Figure 2:
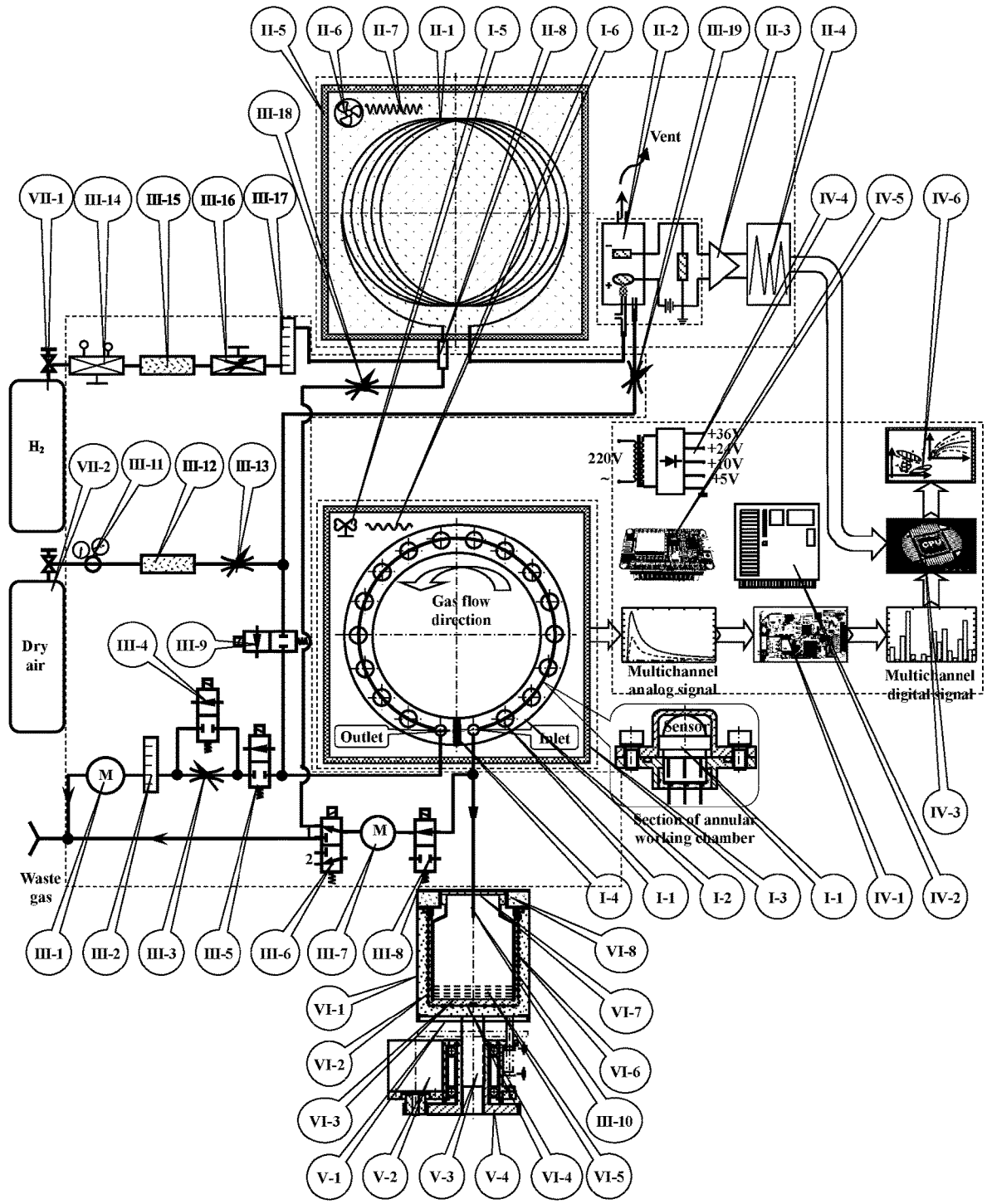
FIG. 2 is a schematic diagram of working principle of the electronic nose instrument, i.e., a schematic diagram of headspace sampling state of the capillary gas chromatographic column, in a method for multi-information fusion of gas sensitivity and chromatography and on-site detection and analysis of flavor substances using an electronic nose instrument provided in the present disclosure.

FIG. 2 is the schematic diagram of working principle of the electronic nose instrument in the headspace sampling state of the capillary gas chromatographic column, in the present disclosure.

Main constructional units of the gas sensor array module I include the gas sensor array I-1, the annular working chamber I-2, the thermal insulation layer I-3, the partition plate I-4, the fan I-5 and the resistance heating element I-6, and is located in the middle right part of the electronic nose instrument. Main constructional units of the capillary gas chromatographic column module II include the capillary gas chromatographic column II-1, the detector II-2, the amplifier II-3, the recorder II-4, a thermal insulation layer II-5, the fan II-6, the resistance heating wire II-7 and the inlet port II-8, and is located in the right upper part of the electronic nose instrument. The gas sensor array module I and the capillary gas chromatographic column module II are used for converting the chemical and physical information of an odor into the electric signals online.

The constructional units of the automatic headspace sampling module III include the first micro vacuum pump III-1, the first flowmeter III-2, the first throttle valve III-3, the first two-position two-port electromagnetic valve III-4, the second two-position two-port electromagnetic valve III-5, the two-position three-port electromagnetic valve III-6, a second micro vacuum pump III-7, the third two-position two-port electromagnetic valve III-8, the fourth two-position two-port electromagnetic valve III-9, the side-hole sampling needle III-10, the first pressure relief valve III-11, the first purifier III-12, the second throttle valve III-13, the second pressure relief valve III-14 and the second purifier III-15, the third throttle valve III-16, the second flowmeter III-17, the fourth throttle valve III-18 and the fifth throttle valve III-19, and is located in the right lower part of the electronic nose instrument.

Main constructional units of the computer control and data analysis module IV include an A/D data acquisition card IV-1, a driving and control circuit board IV-2, a computer mainboard IV-3, a 4-path precision DC stabilized power supply IV-4, a WIFI board card IV-5 and a displayer IV-6, and is located in the left side of the electronic nose instrument. The role of the WIFI board card IV-5 is to real-time transmit the sensitive information of the gas sensor array module I and the capillary gas chromatographic column module II to multiple specified fixed/mobile terminals.

Main constructional units of the automatic lifter V include the support disc V-1, the step motor V-2, the screw mechanism V-3 and the gear transmission mechanism V-4, and is located in the right front lower part of the electronic nose instrument. Main constructional units of the large-volume headspace vapor generation device VI include the thermal insulation layer VI-1, the resistance heating wire VI-2, the heat conduction sleeve VI-3, the temperature sensor VI-4, the tested sample VI-5, the 250 ml glass sample bottle VI-6, the silicone rubber sealing sheet VI-7 and the cup cover VI-8. One electronic nose instrument is equipped with 4-6 large-volume headspace vapor generation devices VI. The role of the large-volume headspace vapor generation device VI is to make 10 ml-30 ml tested sample within the 250 ml glass sample bottle VI-6 at the constant temperature of 40-80±0.1° C. for about 30 min in a certain test site and generate 220 ml-240 ml headspace vapor. The role of the automatic lifter V is to make the headspace vapor generation device VI up 20 mm within 3 s, in order the side-hole sampling needle III-10 fixed under the inlet port of the annular working chamber I-2 penetrate through the silicone rubber sealing sheet VI-7 on 250 ml glass sample bottle VI-6 and thus contact with the headspace vapor in the glass sample bottle VI-6.

Figure 3:
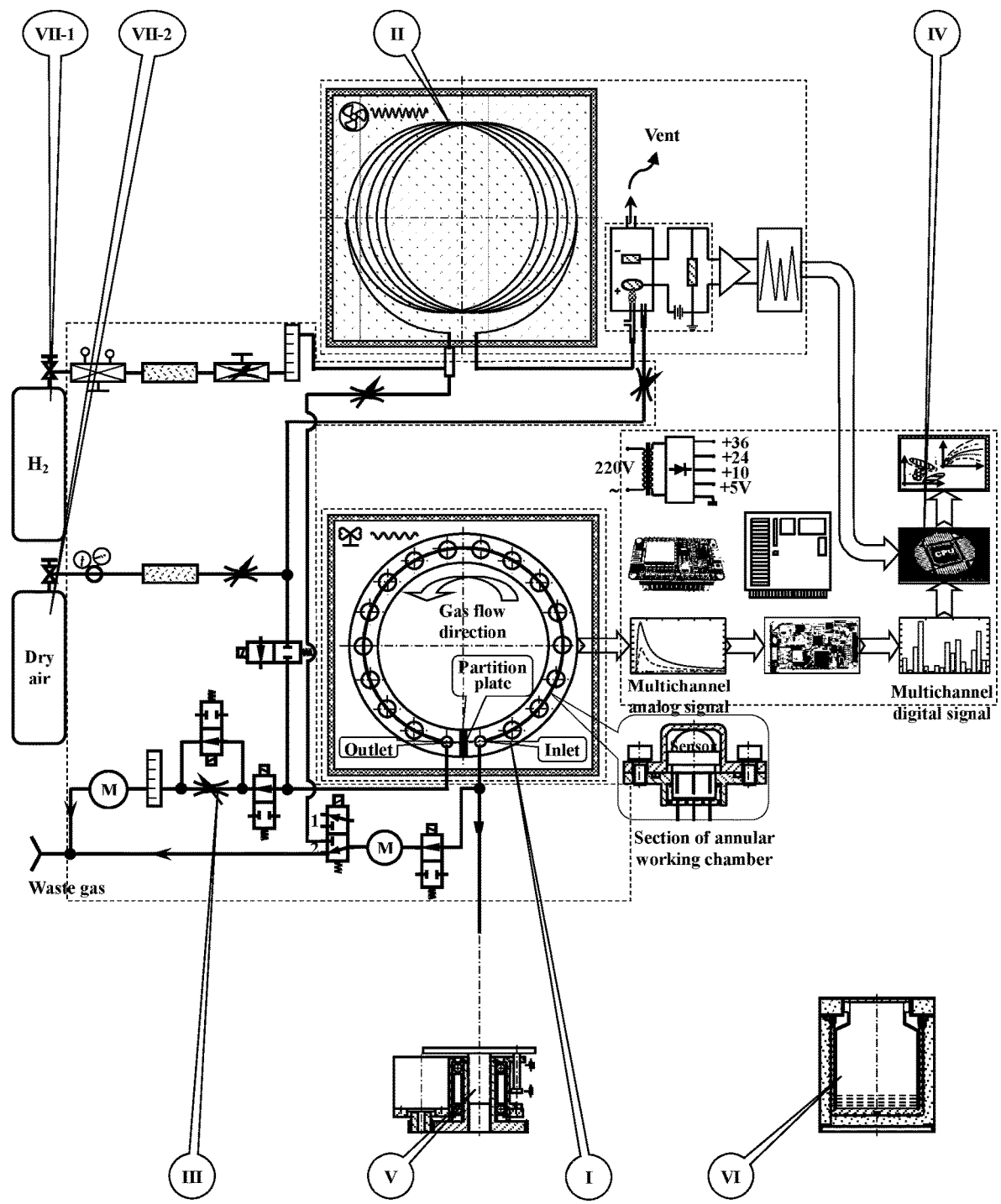
FIG. 3 is a schematic diagram of working principle of the electronic nose instrument, i.e., a schematic diagram of a rough recovery state of a gas sensor array and a separation state of a capillary gas chromatographic column, in a method for multi-information fusion of gas sensitivity and chromatography and on-site detection and analysis of flavor substances using an electronic nose instrument provided in the present disclosure.
Figure 4:
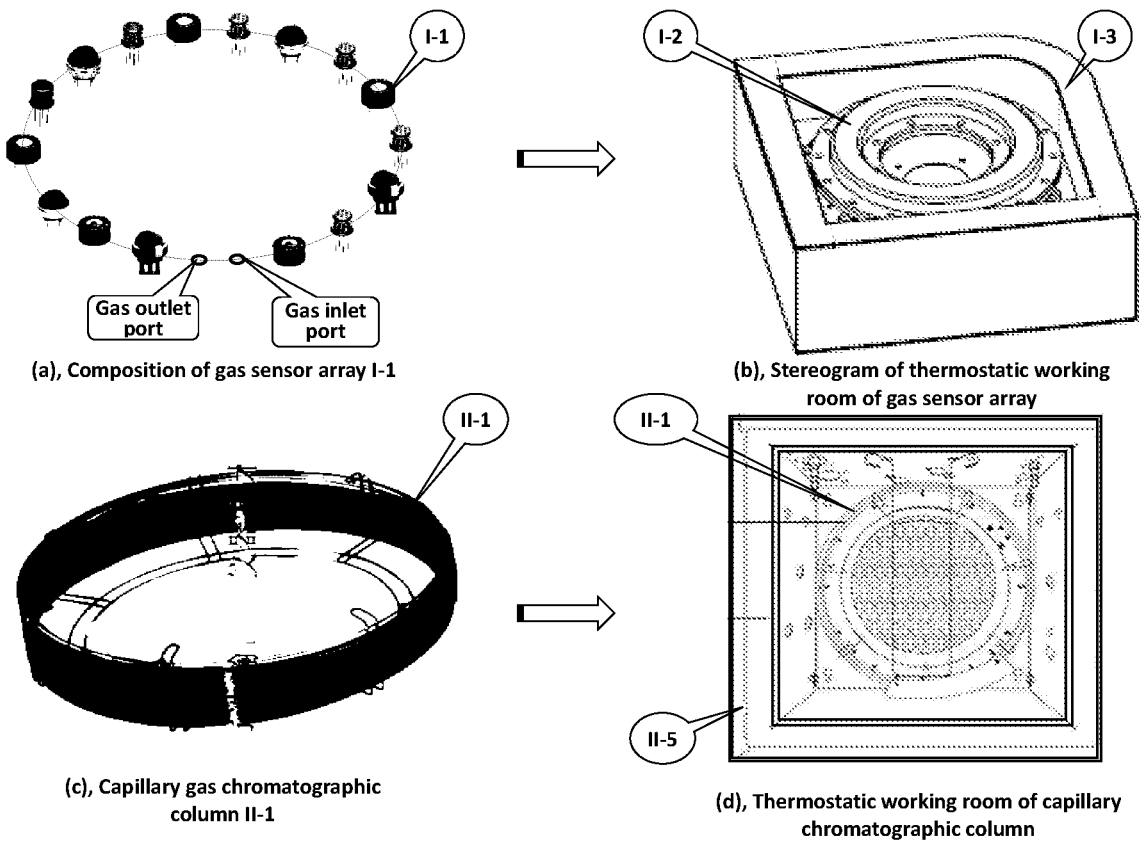
FIG. 4 is a schematic structural diagram of a gas sensor array module and a capillary gas chromatographic column module in a method for multi-information fusion of gas sensitivity and chromatography and on-site detection and analysis of flavor substances using an electronic nose instrument provided in the present disclosure.

FIG. 3 is the schematic diagram of working principle of an electronic nose instrument, i.e., the schematic diagram of the rough recovery state of the gas sensor array and the separation state of the capillary gas chromatographic column. FIG. 4 is the schematic diagram of the gas sensor array module I and the capillary gas chromatographic column module II, which may be easily replaced as needed. At this moment, under the action of the automatic lifter V, the large-volume headspace vapor generation device VI descends 20 mm to the original position along with the support disc V-1 and then is taken away by an operator, and the preparation is made for replacing a new headspace vapor generation device and detecting a new sample.

Figure 5:
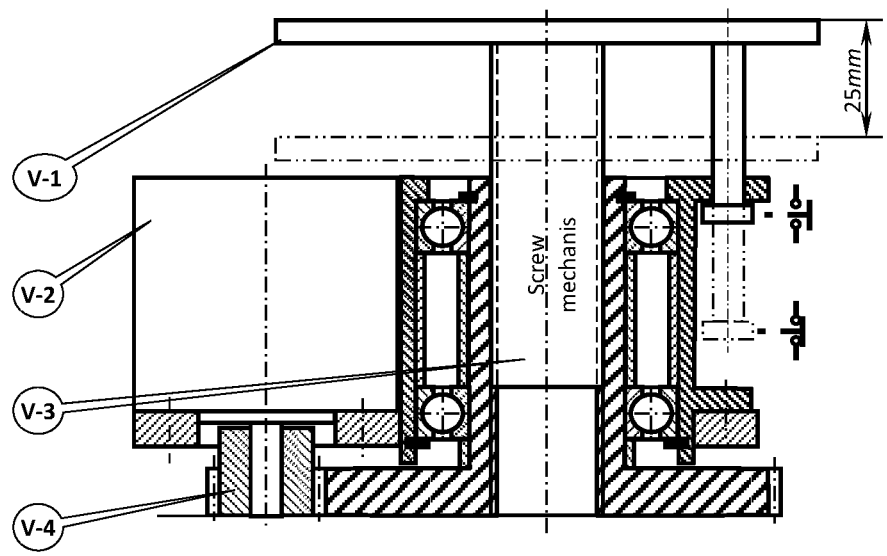
FIG. 5 is a schematic diagram of the automatic lifter for headspace sampling in a method for multi-information fusion of gas sensitivity and chromatography and on-site detection and analysis of flavor substances using an electronic nose instrument provided in the present disclosure.

FIG. 5 gives the detailed structure of the automatic lifter V. The ratio of gear tooth numbers in the gear transmission mechanism V-4 is 17:73, and the gear module is 1 mm. The step motor V-2 drives the screw of the screw mechanism V-3 to ascend through the gear transmission mechanism V-4, so that the large-volume headspace vapor generation device VI placed on the support disc V-1 ascends.

Figure 6:
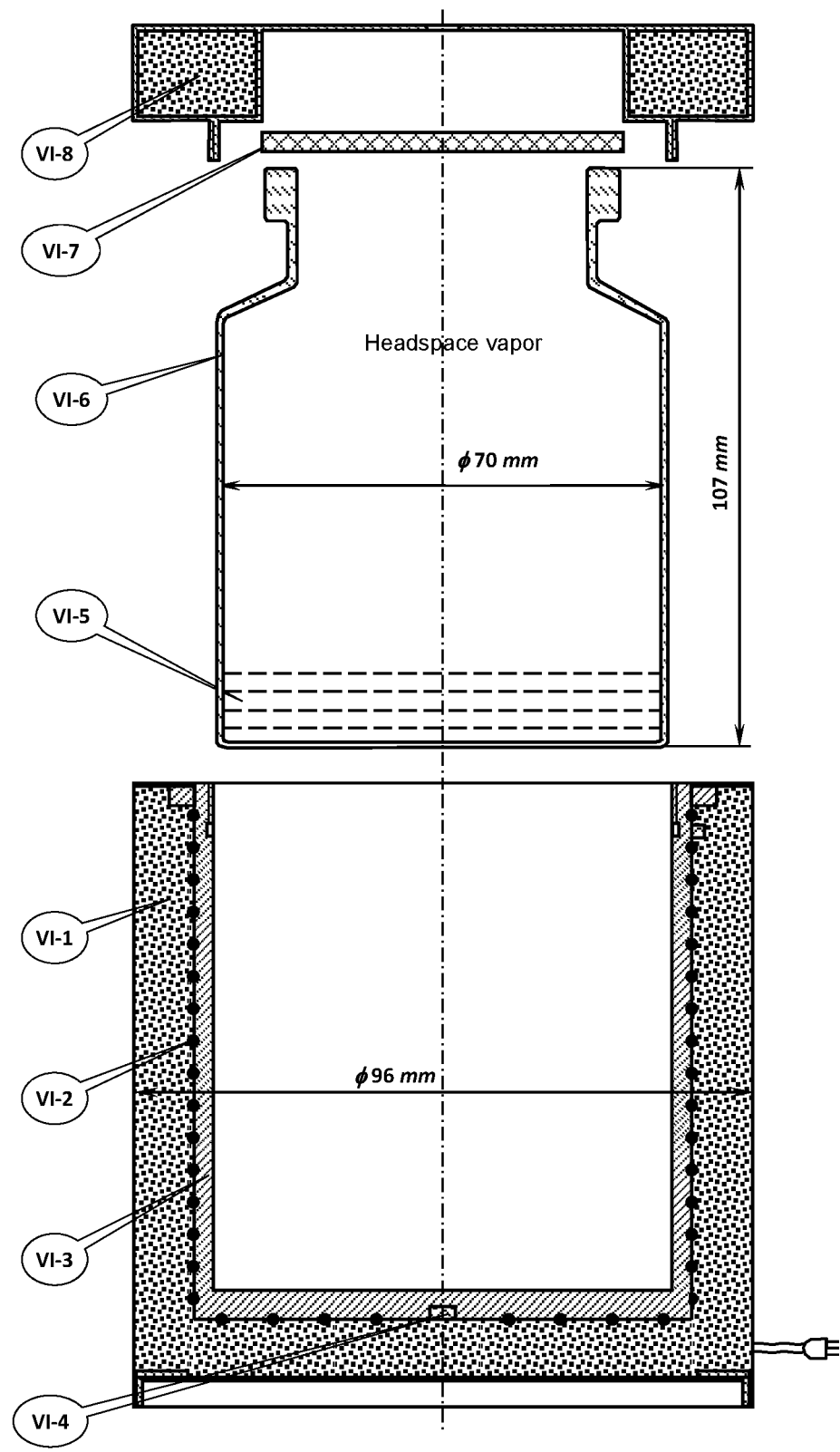
FIG. 6 is a schematic diagram of the headspace vapor generation device in a method for multi-information fusion of gas sensitivity and chromatography and on-site detection and analysis of flavor substances using an electronic nose instrument provided in the present disclosure.

FIG. 6 is the schematic diagram of the mutual positional relationship and the detailed structure of the large-volume headspace vapor generation device VI. When testing, the operator takes 10-30 ml liquid or solid tested sample VI-5 to place in the 250 ml glass sample bottle VI-6, covers the bottle mouth with the silicone rubber seal sheet VI-7, and tightens the cup cover VI-8. Under the heating action of the resistance heating wire VI-2 which is controlled by the computer control and data analysis module IV, the tested sample VI-5 is kept at the constant temperature of 40-80±0.1° C. about 30 min to ensure the consistency of multiple tests.

Figure 7:
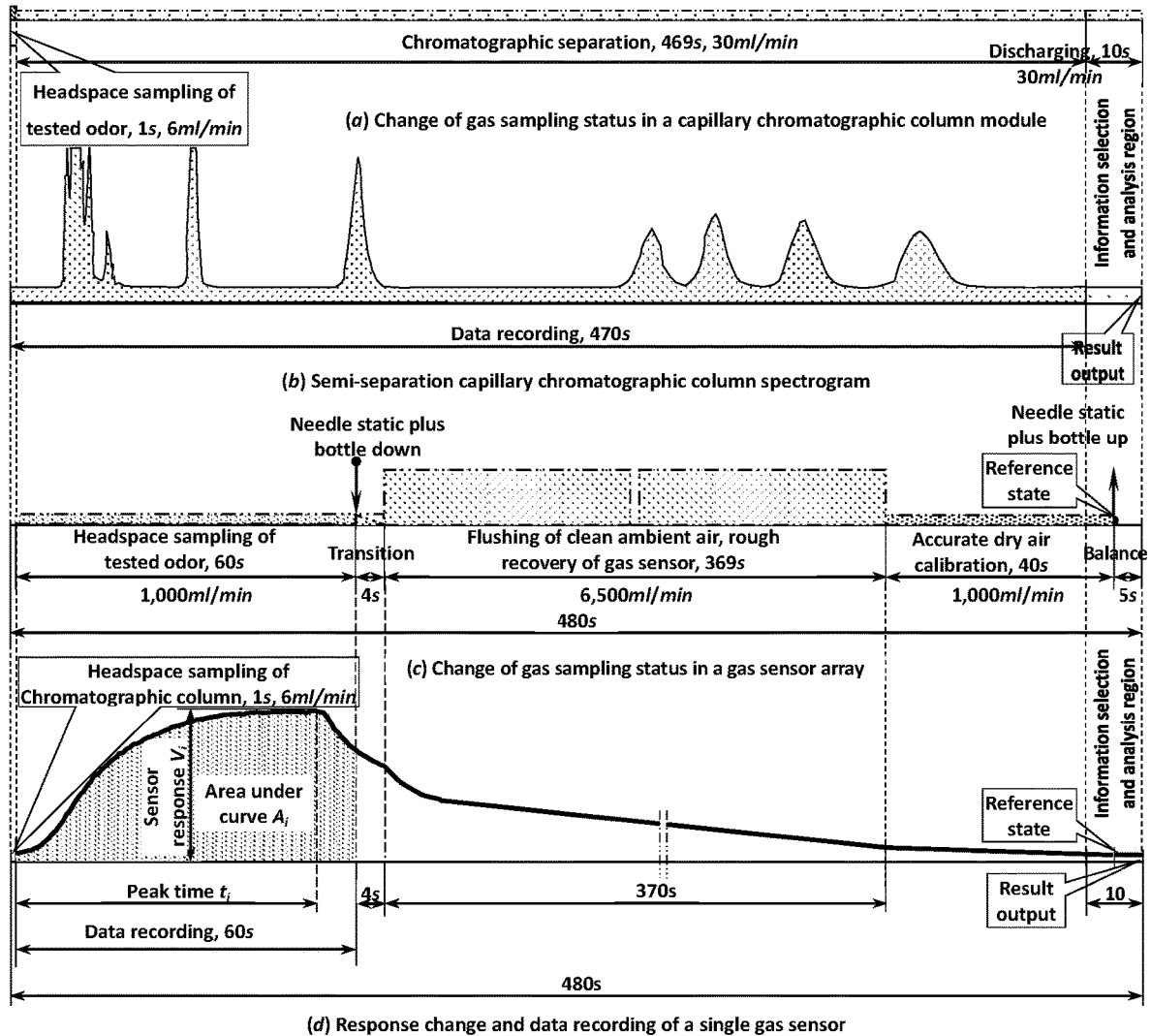
FIG. 7 is a schematic diagram of changes in gas sampling time points, flow rates, and sensitive responses of a capillary chromatographic column module and a gas sensor array module in a gas sampling period T=480 s in a method for multi-information fusion of gas sensitivity and chromatography and on-site detection and analysis of flavor substances using an electronic nose instrument provided in the present disclosure.

FIG. 7 are the schematic diagrams of changes about the gas sampling time lengths, the flow rates and the responses of a specified gas sensor given by the gas sensor array module I and the capillary gas chromatographic column module II in the electronic nose instrument in the gas sampling period T=480 s. The gas sampling period may be adjusted in the range of T=5 min and T=10 min. FIG. 7 only uses the default gas sampling period T=480 s as an example. The adjustable time length is mainly the flushing stage of the ambient air or the rough recovery stage of the gas sensor array module I, and the separation stage of the capillary gas chromatographic column module II. For the gas sensor array module I and the capillary gas chromatographic column module II, the information selection and analysis are performed simultaneously in the last 10s stage of the gas sampling period T.

FIG. 7(*a*) shows the change of cyclical gas sampling cases for the capillary chromatographic column module II, which includes such 3 stage: (i) the tested gas sampling stage, (ii) the tested gas separation stage, and (iii) the chromatographic column discharging stage. The tested gas sampling stage (i) is at a beginning stage of the gas sampling period with a sampling duration of 0.5 s~1.0 s, and is by default. The range of the sampling flow rates is 1.5 ml/min~15 ml/min, 6 ml/min by default.

Referring to FIG. 7, and in combination with FIG. 2, Table 2 shows the operation parameters and the on-off states of the related electromagnetic valves of the capillary gas chromatographic column module II in the gas sampling period T=480 s. In the tested gas sampling stage (i), the two-position three-port electromagnetic valve III-6 is located at "1", the third two-position two-port electromagnetic valve III-8 is on, and the second two-position two-port electromagnetic valve III-5 and the fourth two-position two-port electromagnetic valve III-9 are off, and the on-off status of the first two-position two-port electromagnetic valve III-4 is irrelevant to at this stage. Under the suction action of the second micro vacuum pump III-7, the headspace vapor of the tested sample VI-5 flows through, at a flow rate of 6 ml/min, the third two-position two-port electromagnetic valve III-8, the two-position three-port electromagnetic valve III-6 and the fourth throttle valve III-18 in order, and then mixes with the carrier gas $H_2$ at the inlet port II-8, flows into the capillary gas chromatographic column II-1 accordingly for 1.0 s. If the sampling flow rate is 6 ml/min and the duration is 1 s, then the accumulated sampling volume for a tested odor is 0.1 ml, which meets the requirement of the optimal sampling volume of the capillary gas chromatographic column. In the tested gas separation stage (ii) and the chromatographic column discharging stage (iii), since the two-position three-port electromagnetic valve III-6 is located at "2", and whether the other two-position two-port electromagnetic valves are on or off is not critical. During this period, under the pushing action of the carrier gas $H_2$, the tested odor is separated in the capillary gas chromatographic column II-1.

Referring to FIG. 6 and in combination with FIG. 1 and FIG. 3, Table 3 shows the operating parameters and the on-off status of the related electromagnetic valve for the gas sensor array module I in the gas sampling period T.

Several main working states of the gas sensor array module I are described below in details by taking the gas sampling period T=480 s as an example.

TABLE 2

Operation parameters and on-off status of the related electromagnetic valves for the capillary gas chromatographic column module II in the gas sampling period T = 300 s-600 s (480 s by default)

| Stage | Description | Duration (s) | Initial time-point (s) | Flow rate (ml/min) | Gas type | 2-position 3-port valve III-6 | 2-position 2-port valve III-8 | 2-position 2-port valve III-4 | 2-position 2-port valve III-5 | 2-position 2-port valve III-9 |
|---|---|---|---|---|---|---|---|---|---|---|
| (i) | Gas sampling | 0.5-1.5 | 0 | 1.5~15 | Tested odor | "1" | On | Irrelevant | Off | Off |
| (ii) | Chromatographic separation | 289-589 | 1 | 30~50 | Tested odor + $H_2$ | "2" | Irrelevant | Irrelevant | Irrelevant | Irrelevant |
| (iii) | Chromatographic column discharging | 10 | 290-590 | 30~50 | $H_2$ | "2" | Irrelevant | Irrelevant | Irrelevant | Irrelevant |

TABLE 3

Operation parameters and on-off status of the electromagnetic valves for the gas sensor array module I in the gas sampling period T = 300 s-600 s (480 s by default)

| Stage | Description | Duration (s) | Initial moment (s) | Flow rate (ml/min) | Gas type | 2-position 2-port valve III-5 | 2-position 2-port valve III-4 | 2-position 2-port valve III-6 | 2-position 2-port valve III-8 | 2-position 2-port valve III-9 |
|---|---|---|---|---|---|---|---|---|---|---|
| (i) | Headspace sampling | 60 | 1 | 1,000 | Tested odor | On | Off | Irrelevant | Off | Off |
| (ii) | Transition | 4 | 61 | 1,000 | Purified air | On | Off | Irrelevant | On | Off |
| (iii) | Rough recovery | 175-475 | 65 | 6,500 | Purified air | On | On | Irrelevant | Irrelevant | Off |
| (iv) | Clean air calibration | 40 | 255-555 | 1,000 | Clean air | Off | Irrelevant | Irrelevant | Irrelevant | On |
| (v) | Balance | 5 | 295-595 | 0 | — | Off | Irrelevant | Irrelevant | Off | Off |

In the headspace sampling stage (i) for the tested odor, namely, the [1 s, 61 s] time stage with a duration of 60 s in the gas sampling period T, the second two-position two-port electromagnetic valve III-5 is on, the first two-position two-port electromagnetic valve III-4, the third two-position two-port electromagnetic valve III-8 and fourth two-position two-port electromagnetic valve III-9 are all off, and the on-off status of the two-position three-port electromagnetic valve III-6 has not effect. Under the suction action of the first micro vacuum pump III-1, headspace vapor of the tested sample flows through, at a flow rate of 1,000 ml/min, the side-hole sampling needle III-10, the gas sensor array I-1 inside the annular working chamber I-2, the second two-position two-port electromagnetic valve III-5, the first throttle valve III-3 and the first flowmeter III-2 in order, and finally is discharged to outdoor for 60 s. During this stage, the gas sensor array I-1 generates a sensitive response to the tested odor.

In the rough recovery stage of the gas sensor array, namely, the clean ambient air flushing stage (iii), and the second two-position two-port electromagnetic valve III-5 and the first two-position two-port electromagnetic valve III-4 are on, the fourth two-position two-port electromagnetic valve III-9 is off, and the on-off status of the third two-position two-port electromagnetic valve III-8 and the two-position three-port electromagnetic valve III-6 has not effect at this stage. The ambient air flows through, at a flow rate of 6,500 ml/min, the side-hole sampling needle III-10, the gas sensor array I-1 inside the annular working chamber I-2, the second two-position two-port electromagnetic valve III-5, the first two-position two-port electromagnetic valve III-4 and the first flowmeter III-2 in order, and finally is discharged to outdoor for 370 s. During this stage, the residual odor molecules on an inner walls of the relevant gas pipelines are washed away, the accumulated heat by the gas sensor array is taken away, and the gas sensor array I-1 is roughly recovered to the reference state under the action of the ambient air.

In the accurate dry air calibration stage (iv), namely the time stage of from $435^{th}$ sec to the $475^{th}$ sec of the gas sampling period T, the fourth two-position two-port electromagnetic valve III-9 is on and the second two-position two-port electromagnetic valve III-5 is off, and the on-off status of the other electromagnetic valves is irrelevant. The dry air in the dry air bottle VII-2 flows through, at the flow rate of 1,000 ml/min, the first pressure reducing valve III-11, the first purifier III-12, the second throttle valve III-13, the fourth two-position two-port electromagnetic valve III-9, the gas sensor array I-1 and the side-hole sampling needle III-10 inside the annular working chamber I-2 in order, and finally is discharged to outdoor for 40 s. During this stage, the gas sensor array I-1 is accurately recovered to the reference state under the role of the dry air.

According to FIGS. 7(a) and 7(d), in the last 10 s stage of the gas sampling period T, the gas sensor array module I and the capillary gas chromatographic column module II enter the information selection and analysis operation region simultaneously for 10 s.

Figure 8:
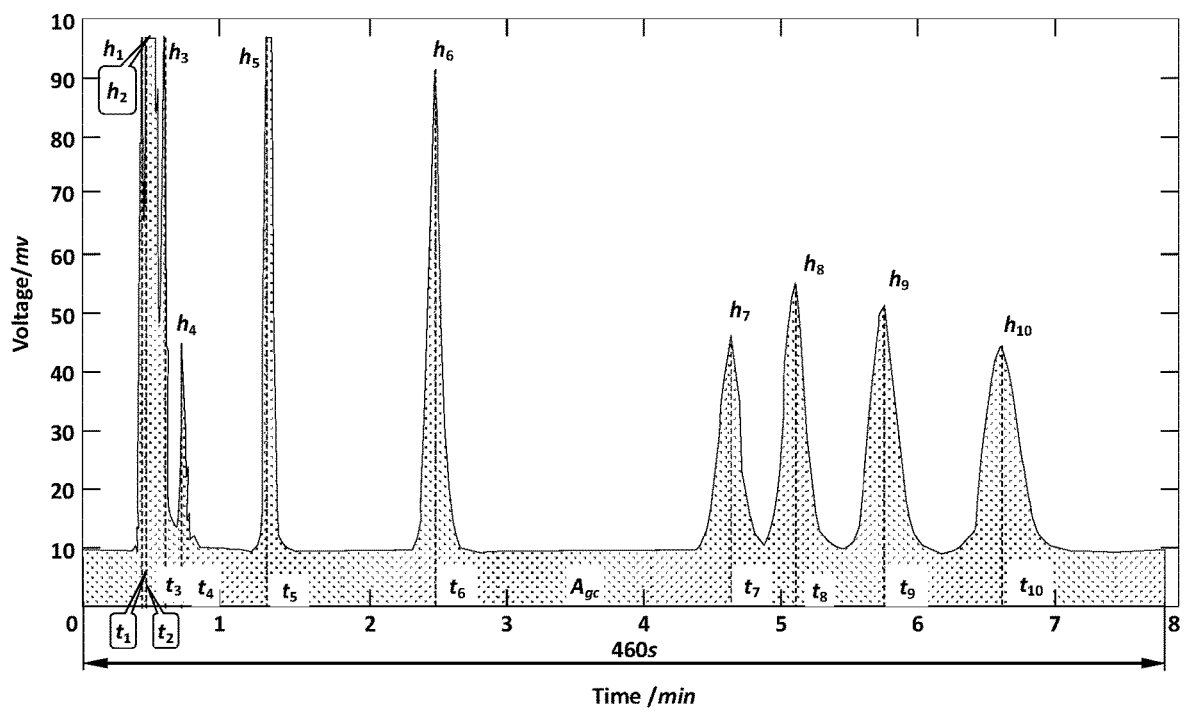
FIG. 8 is a schematic diagram of multi-information selection of a semi-separated chromatogram in a gas sampling period T=480 s in a method for multi-information fusion of gas sensitivity and chromatography and on-site detection and analysis of flavor substances using an electronic nose instrument provided in the present disclosure.

FIG. 8 is the schematic diagram of information selection of the semi-separated chromatogram in the gas sampling period T=480 s. In the information selection and analysis region of 10 s in the gas sampling period T, the computer control and data analysis module IV sequentially selects 21 feature variables: 10 pairs of {peak height $h_{gcj}$, retention time point $t_{gcj}$} (j=1, 2, . . . , 10) and one under-curve area $A_{gc}$ from the semi-separated chromatogram with the appointed 460 s time length, which are the basic sensitive information of the capillary chromatographic column module II to the tested odor and are recorded as $x_{gc}$= {($h_{gc1}$, $h_{gc2}$, . . . , $h_{gc10}$); ($t_{gc1}$, $t_{gc2}$, . . . , $t_{gc10}$); $A_{gc}$}.

Figure 9:
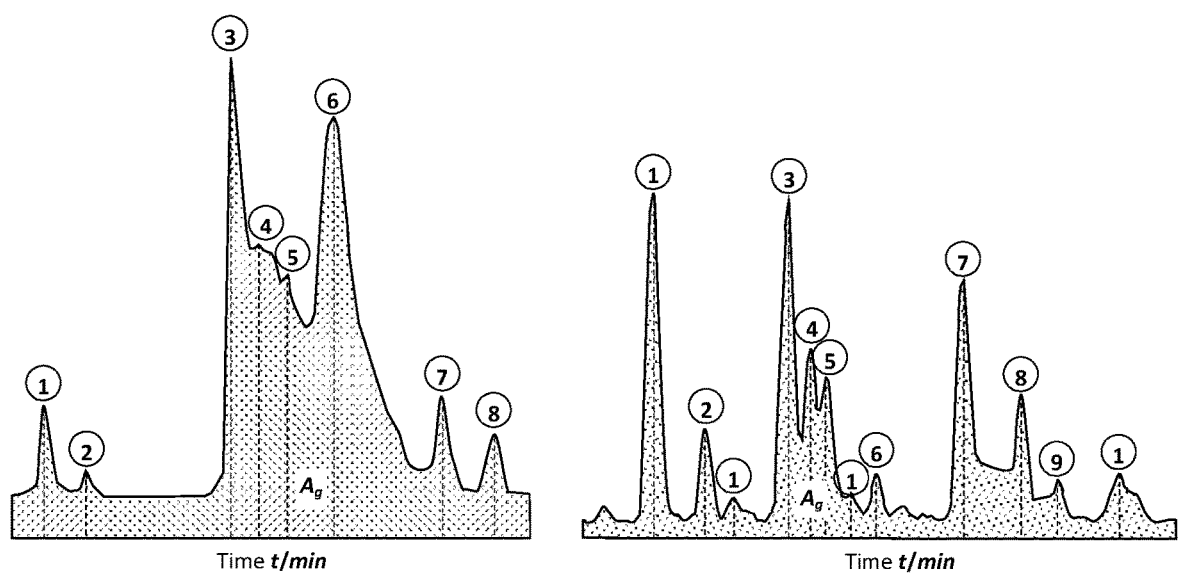
FIG. 9 is a schematic diagram of feature selection of two semi-separated chromatograms in a gas sampling period T=480 s in a method for multi-information fusion of gas sensitivity and chromatography and on-site detection and analysis of flavor substances using an electronic nose instrument provided in the present disclosure.

FIG. 9 is the schematic diagram of feature selection of two semi-separated chromatograms in the gas sampling period T=480 s. The semi-separated chromatogram in FIG. 9(a) has only 8 chromatographic peaks, or only 8 peaks $h_{gci}$(i=1, 2, . . . , 8) and the corresponding 8 retention time values $t_{gci}$(i=1, 2, . . . , 8) and plus the under-curve area $A_{gc}$ are obtained from the semi-separated chromatogram. Our practice is to fill '0's elements for the insufficient chromatographic peaks and the corresponding retention time values. Through doing so, the final chromatographic sensitive information is $x_{gc}$={($h_{gc1}$, $h_{gc2}$, . . . , $h_{gc8}$, 0, 0); ($t_{gc1}$, $t_{gc2}$, . . . , $t_{gc8}$, 0, 0); $A_{gc}$} according to FIG. 9(a). The semi-separated chromatogram in FIG. 9(b) has more than 10 chromatographic peaks, and thus the top 10 maximum chromatographic peaks are selected from them.

Figure 10:
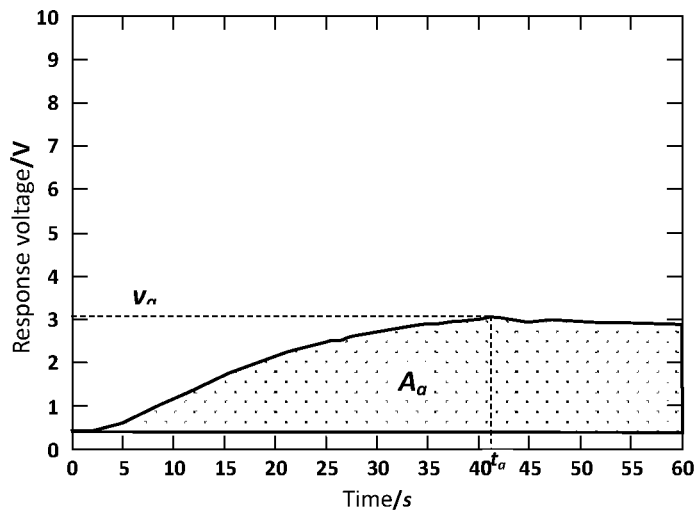
FIG. 10 is a schematic diagram of multi-feature selection of a gas sensor response curve in a gas sampling period T=480 s in a method for multi-information fusion of gas sensitivity and chromatography and on-site detection and analysis of flavor substances using an electronic nose instrument provided in the present disclosure.
Figure 10:
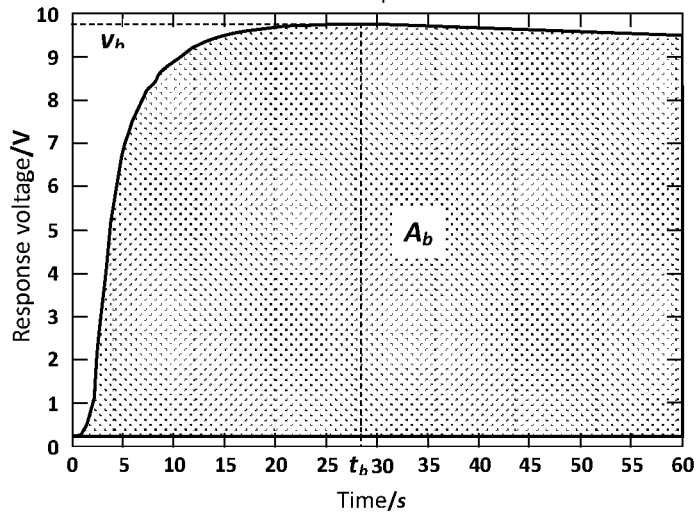
Figure 10:
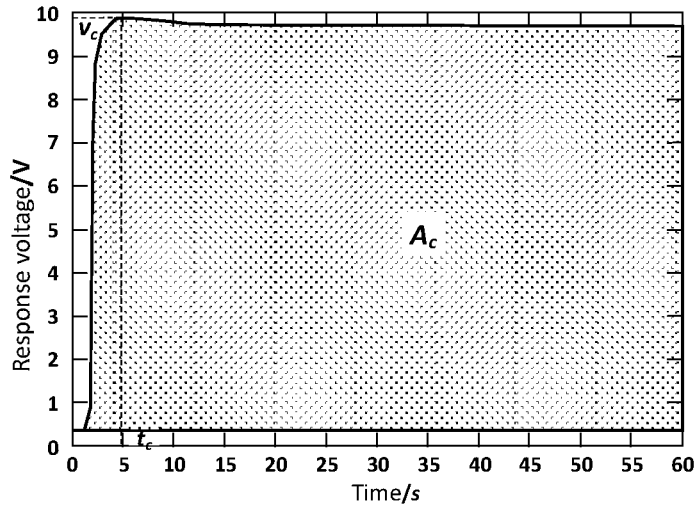
Figure 11:
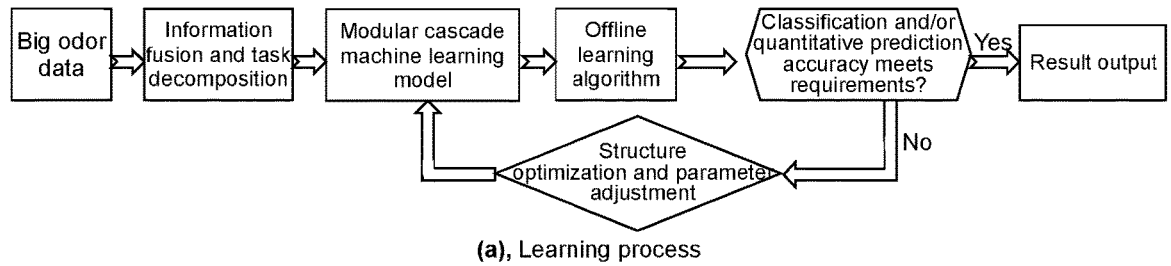
FIG. 11 is a schematic diagram of an offline learning and online decision-making process in a machine learning model in a method for multi-information fusion of gas sensitivity and chromatography and on-site detection and analysis of flavor substances using an electronic nose instrument provided in the present disclosure.
Figure 11:
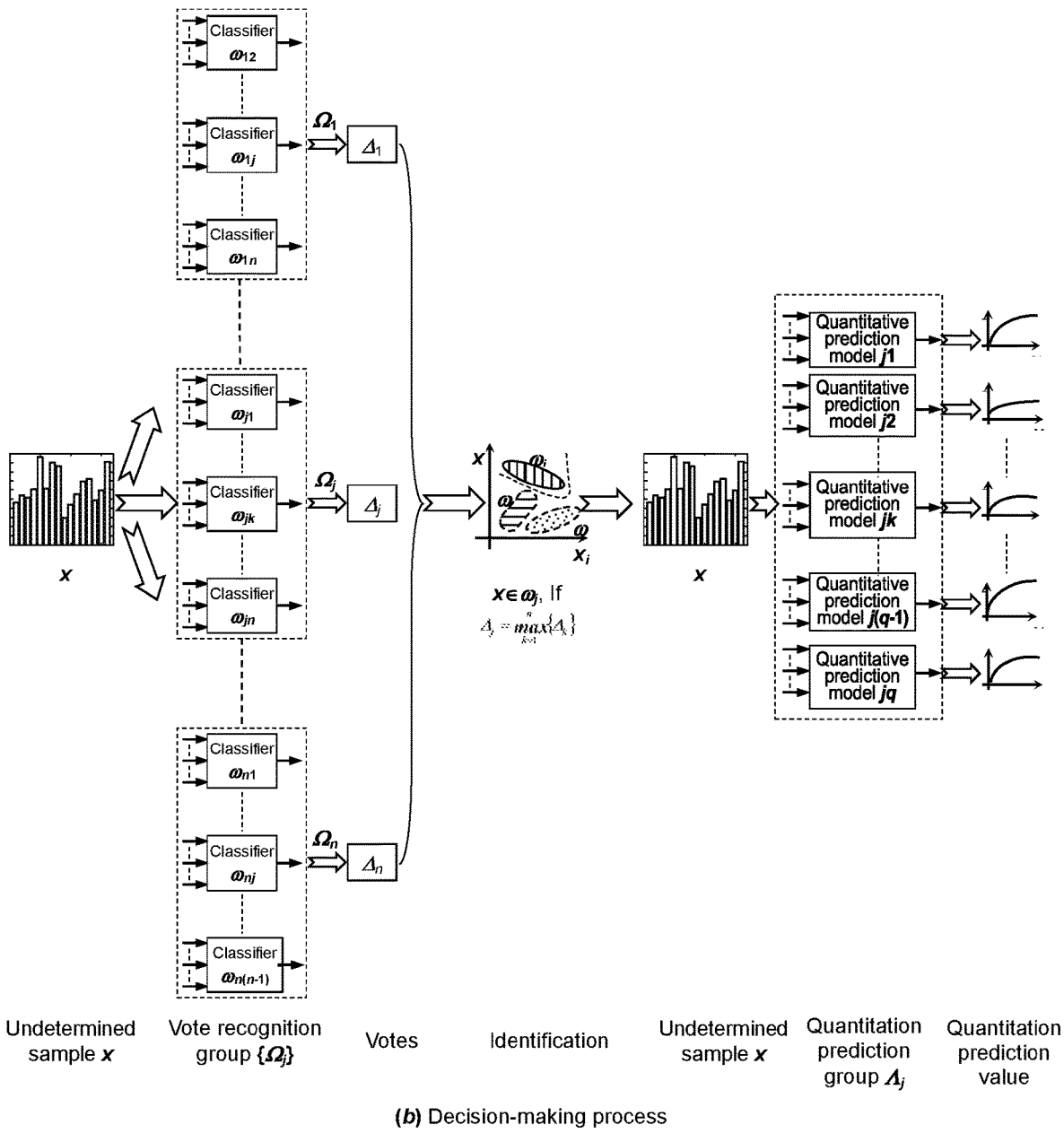

FIG. 10 is the schematic diagram of multi-feature selection of response curves of gas sensors in the gas sampling period T=480 s. Three illustrations in FIG. 10 respectively show the response curves of 3 gas sensors, TGS822, TGS826 and TGS832, for a petroleum wax sample, a 2,000 ppm ethylene gas and a 5,000 ppm ethanol vapor. The steady-state maximum voltage response values in FIGS. 10(b) and 10(c) are equal, or $v_b$=$v_c$. According to the conventional feature selection method of the single steady-state maximum value from a single voltage response curve, the electronic nose instrument cannot distinguish the 2,000 ppm ethylene gas and the 5,000 ppm ethanol vapor at that time. After careful observation, it is found that FIG. 10(b) and FIG. 10(c) show such a case, called 'Case 1': although the voltage response steady-state maximum response values in the two diagrams are equal, the corresponding peak time values and the under-curve area are not equal. Similarly, Case 2 shows that the corresponding peak time values are equal to one another, but their peak values and the under-curve areas are not equal. Case 3 shows that the under-curve areas are equal to one another, but their peak values and the corresponding peak time values are not equal.

information of the gas sensor array. Furthermore, the recognition, qualitative analysis and main component quantitative prediction of an undermined odor are realized by means of the artificial intelligence or machine learning method. FIG. 11 is the schematic diagram of offline learning and online decision-making process of the modular cascade machine learning model adopted in the present disclosure.

TABLE 4

Comparison of the main operation parameters between the gas sensor array module I and the capillary gas chromatographic column module II (taking the gas sampling period T = 8 min as an example)

| Module name | Headspace duration (s) | Starting time-point (s) | Flow rate (ml/min) | Sampling manner | Carrier | Fuel gas | Chamber temperature (° C.) | Information selection and analysis time length (s) | Meaning of information components | Module size (mm) |
|---|---|---|---|---|---|---|---|---|---|---|
| capillary gas chromatographic column | 0.5-1.5 | 0 | 1.5-15 | Automatic | $H_2$ | $H_2$ | 200-250 | 470-480 | 10 peak heights, 10 retention time-points, one under-curve area | 300 × 300 × 120 |
| Gas sensor array | 30~60 | 1 | 1,000 | Automatic | None | None | 55 | 470-480 | 16 peak voltages, 16 peak time-points, 16 under-curve areas | 300 × 300 × 100 |

According to FIG. 10, the present disclosure proposes the following viewpoint: three pieces of information, i.e., a steady-state maximum voltage response $v_{gsi}$, a corresponding peak time value $t_{gsi}$ from the starting moment of the headspace sampling, and an area $A_{gsi}$ under the curve in the 60 s headspace sampling time stage, are selected simultaneously from the response curve of the gas sensor i. If the gas sensor array is composed of 16 sensitive elements, then in the 10s information selection and analysis region of the gas sampling period T, the computer control and data analysis module IV sequentially selects 3*16=48 feature values from 16 response curves as the basic sensitive information of the gas sensor array module I to the tested odor, which is recorded as $x_{gs}=\{(v_{gs1}, v_{gs2}, \ldots, v_{gs16}); (t_{gs1}, t_{gs2}, \ldots, t_{gs16}); (A_{gc1}, A_{gc2}, \ldots, A_{gc16})\}$.

In the 10 s information selection and analysis region of the gas sampling period T, the computer control and data analysis module IV fuses the sensitive information of the gas sensor array module I and the capillary chromatographic column module II in different time stages to the tested odor, and then performs the normalization pretreatment to obtain a sensitive information vector of the electronic nose instrument to the tested sample, i.e., $x=x_{gs}+x_{gc}=\{(v_{gs1}, v_{gs2}, \ldots, v_{gs16}); (t_{gs1}, t_{gs2}, \ldots, t_{gs16}); (A_{gc1}, A_{gc2}, \ldots, A_{gc16}); (h_{gc1}, h_{gc2}, \ldots, h_{gc10}); (t_{gc1}, t_{gc2}, \ldots, t_{gc10}); A_{gc}\} \in R^{69}$. The sensitive vector $x \in R^{69}$ is the basis of online identification of types and quantitative prediction of main components by the electronic nose instrument for foods, condiments, fragrances and flavors, and petroleum waxes.

Table 4 shows the comparison of the main operation parameters between the gas sensor array module I and the capillary gas chromatographic column module II by taking the gas sampling period T=8 min as an example. In comparison with the 60 s sampling duration and the 1,000 ml/min flow rate of the former, the corresponding terms of the latter are only 1 s and 6 ml/min. According to the above data, the gas sampling volume of the gas sensor array module I is 1,000 ml, but that of the capillary gas chromatographic column module II is only 0.1 ml, or the difference between the two is 10,000 times.

In the present disclosure, the semi-separated chromatogram is regarded as a part of the sensitive information or pattern of the electronic nose instrument, and thus the big odor data is established by combining with the sensitive In the offline learning stage of the modular cascade machine learning model, the primary task is to establish the big odor data, including the online sensitive data of the gas sensor array module I and the capillary gas chromatographic column module II for a large number of foods, condiments, fragrances and flavors, and petroleum waxes, the offline measuring data of the conventional instruments such as gas chromatography/mass spectrometry; the label data and the sensory evaluation data for the known types and constituents of odors.

Next, the sensitive data of both the gas sensor array and the capillary gas chromatographic column are fused, including the normalization and dimensionality reduction preprocessing. In order to reduce the analysis difficulty of the big odor data, the present disclosure employs the "divide and conquer" strategy, (i), a complex multi-type recognition problem is decomposed into multiple simpler two-odor recognition problems, that is, one n-class problem is decomposed into $n(n-1)/2$ binary-class problems $\{X_j, X_k\}$ and then solved by $n(n-1)/2$ single-output machine learning models $\{\omega_{jk}\}_n$, where j, k=1, 2 . . . , n and j≠k, one by one; and (ii) a complex multi-component estimation problem is decomposed into multiple simpler single-component quantitative prediction problems, one by one, that is, a q-curve/q-surface fitting problem is decomposed into q curve/surface fitting problems, and q single-output machine learning models are used for solving them, one by one.

The $n(n-1)/2$ single-output machine learning models $\omega_{jk}$ (j, k=1, 2, . . . , n and j≠k) in the first level and the q single-output machine learning models in the second level form the modular cascade machine learning model. Among them, each single-output machine learning model both in the first level and in the second level may be one single-output single-hidden-layer neural network, one decision tree, one support vector machine, etc. Here, the present disclosure employs single-output single-hidden-layer neural networks. The offline learning algorithm of the modular cascade machine learning model is mainly the error back-propagation algorithm, which mainly learns the labeled data and the data with the known constituents in the big odor data.

In the decision-making stage, the $n(n-1)/2$ single-output machine learning models in the first level form n vote recognition groups $\{\Omega_j\}_n$, j=1, 2, . . . , n. A single-output machine learning model takes and only takes part in two vote recognition groups. For example, the single-output single-hidden-layer neural network $\omega_{jk}$ votes not only in the vote recognition group $\Omega_j$ but also in the group $\Omega_k$. The undetermined pattern x belongs to the class represented by the vote recognition group with the most votes, i.e., the winning vote recognition group. Then, the quantitative prediction group corresponding to the winning vote recognition group in the second level predicts multiple quantitative indicator values of the tested odor x, i.e., the overall intensity, the quality grade and the concentrations of multiple main components.

What is claimed is:

1. A method for multi-information fusion of gas sensitivity and chromatography and on-site detection and analysis of flavor substances using an electronic nose instrument, wherein the electronic nose instrument comprises a gas sensor array module I, a capillary gas chromatographic column module II, an automatic headspace sampling module III, a computer control and data analysis module IV, an automatic lifter V for headspace sampling, a large-volume headspace vapor generation device VI and two auxiliary gas sources VII-1 and VII-2, which are configured to implement an on-site real-time detection and intelligent analysis of such flavor substances as foods, condiments, fragrances and flavors, and petroleum waxes; wherein, the gas sensor array module I comprises a gas sensor array I-1, an annular working chamber I-2 for installing the gas sensor array I-1, a thermal insulation layer I-3, a partition plate I-4, a fan I-5 and a resistance heating element I-6, and is located in a middle right part of the electronic nose instrument;

the capillary gas chromatographic column module II comprises a capillary gas chromatographic column II-1, a detector II-2, an amplifier II-3, a recorder II-4, a thermal insulation layer II-5, a fan II-6, a resistance heating wire II-7 and an inlet port II-8, and is located in a right upper part of the electronic nose instrument;

the automatic headspace sampling module III comprises a first micro vacuum pump III-1, a first flowmeter III-2, a first throttle valve III-3, a first two-position two-port electromagnetic valve III-4, a second two-position two-port electromagnetic valve III-5, a two-position three-port electromagnetic valve III-6, a second micro vacuum pump III-7, a third two-position two-port electromagnetic valve III-8, a fourth two-position two-port electromagnetic valve III-9, a side-hole sampling needle III-10, a first pressure relief valve III-11, a first purifier III-12, a second throttle valve III-13, a second pressure relief valve III-14, a second purifier III-15, a third throttle valve III-16, a second flowmeter III-17, a fourth throttle valve III-18 and a fifth throttle valve III-19, and is located in a right lower part of the electronic nose instrument;

main constructional units of the computer control and data analysis module IV comprise an A/D data acquisition card IV-1, a driving and control circuit board IV-2, a computer mainboard IV-3, a 4-path precision DC stabilized power supply IV-4, a WIFI board card IV-5 and a display IV-6, and is located in a left side of the electronic nose instrument;

main constructional units of the automatic lifter V for headspace sampling comprise a support disc V-1, a step motor V-2, a screw mechanism V-3 and a gear transmission mechanism V-4, and is located in a right front lower part of the electronic nose instrument;

main constructional units of the large-volume headspace vapor generation device VI comprise a thermal insulation layer VI-1, a resistance heating wire VI-2, a heat conduction sleeve VI-3, a temperature sensor VI-4, a tested sample VI-5, a 250 ml glass sample bottle VI-6, a silicone rubber sealing sheet VI-7 and a cup cover VI-8; one electronic nose instrument is provided with 4-6 large-volume headspace vapor generation devices VI, and the role of the large-volume headspace vapor generation device VI is to make 10 ml-30 ml tested sample within the 250 ml glass sample bottle VI-6 at a constant temperature of 40-80±0.1° C. for about 30 min in a test site, and generate 220 ml-240 ml headspace vapor; the automatic lifter V is employed to make the large-volume headspace vapor generation device VI up 20 mm within 3 s, so that the side-hole sampling needle III-10 fixed under a gas inlet port of the annular working chamber I-2 penetrates through a silicone rubber sealing sheet VI-7 and contacts with headspace vapor in the 250 ml glass sample bottle VI-6; and a gas sampling period of a headspace vapor for the tested sample VI-5 by the electronic nose instrument is T-300-600 s, and T=480 s by default; in a gas sampling period T, setting the sampling time of a tested headspace vapor of the capillary gas chromatographic column module II to be earlier than that of the gas sensor array module I; in a case of T=480 s, setting the default headspace vapor sampling time of the capillary gas chromatographic column module II to be 1 s earlier than that of the module I; setting the default ratios of a flow rate, a sampling duration and an accumulated sampling volume of the gas sensor array module I to the capillary gas chromatographic column module II for a tested odor sample to be 1,000:6 ml/min, 60:1 s and 1,000:0.1 ml (theoretical value) in order; and performing, by the computer control and data analysis module IV, a sensitive information selection and analysis operation on the gas sensor array module I and the capillary gas chromatographic column module II simultaneously;

in the gas sampling period T, pumping, by the first micro vacuum pump III-1 and the second micro vacuum pump III-7, the headspace vapor into the gas sensor array module I and the capillary gas chromatographic column module II, respectively, so that the gas sensor array I-1 and the capillary gas chromatographic column II-1 generate a sensitive response, respectively; obtaining, by the electronic nose instrument, 1 group of gas sensor response curves and 1 gas chromatogram to serve as an analog signal of gas sensitivity and gas chromatography obtained by perceiving an odorous sample by the electronic nose instrument;

in the gas sampling period T, extracting, by the computer control and data analysis module IV, 48 response information variables from a plurality of response curves of the gas sensor array module I, selecting 21 feature information variables from a finite-duration semi-separated chromatogram of the capillary gas chromatographic column module II, and therefore obtaining, by the electronic nose instrument, a 69-dimensional response vector $x(\tau) \in R^{69}$, which is referred to as a pattern hereinafter; saving the response vector in a corresponding data file of a hard disk in the computer mainboard IV-3; and sending the pattern data to a cloud terminal and many specified fixed/mobile terminals through a WIFI routing module;

on-site detecting, by the electronic nose instrument, various flavor substances such as foods, condiments, fragrances and flavors, and petroleum waxes for a long time over many months and years to form an big odor data X, and establishing, by a part of data of the big odor data X, a corresponding relation between a gas sensitivity/gas chromatography response and an odor type, an intensity grade and main component concentrations of the flavor substances; and in a learning stage, learning, by a cascade machine learning model of the computer control and data analysis module IV, a normalized pre-processing big odor data X offline to determine the structure and parameters of the cascade machine learning model, and learning a gas sensitivity/gas chromatography recent response online to finely tune the parameters of the cascade machine learning model; in a decision-making stage, online determining, by the cascade machine learning model, types of various foods, condiments, fragrances and flavors, and petroleum waxes according to a gas sensitivity/gas chromatography current response vector $x(\tau)$, and quantitatively predicting an intensity grade and main component concentration values of odors.

2. The method for multi-information fusion of gas sensitivity and chromatography and on-site detection and analysis of flavor substances using an electronic nose instrument of claim 1, wherein the gas sensor array I-1 and the annular working chamber I-2 are located in a thermostatic working room of 55±0.1° C.; in the gas sampling period T, the gas sensor array module I goes through: (i) a headspace sampling stage of the capillary gas chromatographic column module II for a tested odor, with a default duration of 1 s, and a default flow rate of 6 ml/min; (ii) a headspace sampling stage of the gas sensor array module I for the tested odor, with a duration of 60 s, and a flow rate of 1,000 ml/min; (iii) a transition stage, with a duration 4 s, a flow rate of 1,000 ml/min for the ambient air; (iv) a flushing stage of the ambient air, namely a rough recovery stage of the gas sensor array, with a duration of T-110 s; v) an accurate dry air calibration stage, with a duration of 40 s; and (vi) a balance stage, i.e., a silent stage without gas flow, with a duration of 5 s, in order; where the "transition stage" realizes the transformation from the tested headspace vapor to the ambient air, and the ambient air is used for a rough recovery of the gas sensor array I-1, a flushing of the annular working chamber I-2 and the inner walls of the related gas pipelines, and a removal of the accumulated heat generated by the gas sensor array.

3. The method for multi-information fusion of gas sensitivity and chromatography and on-site detection and analysis of flavor substances using an electronic nose instrument of claim 1, wherein an [1 s, 61 s] interval of the gas sampling period T is the headspace sampling stage of the gas sensor array module I for a tested odor; in this stage, setting the second two-position two-port electromagnetic valve III-5 to be on, and setting the first two-position two-port electromagnetic valve III-4, the third two-position two-port electromagnetic valve III-8 and the fourth two-position two-port electromagnetic valve III-9 to be off, whether the two-position three-port electromagnetic valve III-6 is on or off has not effect at the moment; under a suction action of the first micro vacuum pump III-1, a headspace vapor generated by the tested sample VI-5 flows through, at a flow rate of 1,000 ml/min, the side-hole sampling needle III-10, the annular working chamber I-2 and the internal gas sensor array I-1, the second two-position two-port electromagnetic valve III-5, the first throttle valve III-3 and the first flowmeter III-2 in order, and finally is discharge to outdoor for 60 s; and during this stage, therefore, generating, by the gas sensor array 1-1, a sensitive response for the tested odor, and saving the response data in a temporary file of the computer mainboard IV-3.

4. The method for multi-information fusion of gas sensitivity and chromatography and on-site detection and analysis of flavor substances using an electronic nose instrument of claim 1, wherein a [T-45 s, T-5 s] interval of the gas sampling period T is the dry air calibration stage of the gas sensor array module I; in this stage, setting the fourth two-position two-port electromagnetic valve III-9 to be on, setting the second two-position two-port electromagnetic valve III-5 to be off; whether the other electromagnetic valves are on or off is irrelevant; and making the dry air in the dry air bottle VII-2 flows through, at a flow rate of 1,000 ml/min, the first pressure relief valve III-11, the first purifier III-12, the second throttle valve III-13, the fourth two-position two-port electromagnetic valve III-9, the gas sensor array I-1 and the side-hole sampling needle III-10 inside the annular working chamber I-2, and finally discharge the dry air to outdoor for 40 s; and during this stage, making the gas sensor array I-1 accurately recover to a reference state under the role of the dry air.

5. The method for multi-information fusion of gas sensitivity and chromatography and on-site detection and analysis of flavor substances using an electronic nose instrument of claim 1, wherein a [65 s, T-45 s] interval of the gas sampling period T is the flushing stage of the ambient air or the rough recovery stage of the gas sensor array; in this stage, setting the second two-position two-port electromagnetic valve III-5 and the first two-position two-port electromagnetic valve III-4 to be on, and setting the second two-position two-port electromagnetic valve III-4 to be off, whether the third two-position two-port electromagnetic valve III-8 and two-position three-port electromagnetic valve III-6 are on or off is irrelevant at the moment; under the suction action of the first micro vacuum pump III-1, making the ambient air flow through, at a flow rate of 6,500 ml/min, the side-hole sampling needle III-10, the annular working chamber I-2 and the gas sensor array I-1, the second two-position two-port electromagnetic valve III-5, the first two-position two-port electromagnetic valve III-4 and the first flowmeter III-2 in order, and finally discharge the ambient air to outdoor for T-110 s; and during this stage, washing away the residual odor molecules on the inner walls of the related gas pipelines, taking away the accumulated heat generated by the long-term work of the gas sensor array, and making the gas sensor array I-1 roughly recover to a reference state under the role of the ambient air.

6. The method for multi-information fusion of gas sensitivity and chromatography and on-site detection and analysis of flavor substances using an electronic nose instrument of claim 1, wherein a commercially available capillary gas chromatographic column II-1 is in a size of length×inner diameter×film thickness=L×ϕd×δ=30 m×ϕ0.53 mm×0.25 μm, and is located in an thermostatic box with a constant temperature of 250-300±0.1° C.; in the gas sampling period T, making the capillary gas chromatographic column module II undergo the following three stages: (i) a headspace sampling stage for a tested odor, with a duration of 1 s (by default), (ii) a gas chromatographic separation stage of T-11 s (by default), and (iii) a discharging, cleaning and purging stage of 10 s, wherein a duration of the headspace sampling stage for the tested odor is 0.5 s~1.0 s, and the default value is 1 s, the range of sampling flow rate is 1.5 ml/min~15 ml/min, and 6 ml/min by default; using $H_2$ in the auxiliary gas source VII-1 as both a carrier gas and a fuel gas, and using the dry air in the auxiliary gas source VII-2 as a combustion-supporting gas;

a [0, 1 s] interval of the gas sampling period T is the headspace sampling stage of the capillary gas chromatographic column module II for the tested odor; in this stage, setting the two-position three-port electromagnetic valve III-6 to be at "1", setting the third two-position two-port electromagnetic valve III-8 to be on, and setting the second two-position two-port electromagnetic valve III-5 and the fourth two-position two-port electromagnetic valve III-9 to be off, whether the first two-position two-port electromagnetic valve III-4 is on or off irrelevant at the moment; under the suction action of the second micro vacuum pump III-7, making the headspace vapor of the tested sample VI-5 flow through, at a flow rate of 1.5 ml/min-15 ml/min, the third two-position two-port electromagnetic valve III-8, the two-position three-port electromagnetic valve III-6 and the fourth throttle valve III-18 in order, and mixing with the carrier gas $H_2$ at the inlet port II-8, whereby flowing into the capillary gas chromatographic column II-1 for 0.1 s-1.5 s; in a case of the sampling flow rate of 6 ml/min and the duration of 1 s, making a cumulative sampling volume of the tested odor be 0.1 ml, and thus meeting an optimal sampling volume requirement of the capillary gas chromatographic column.

7. The method for multi-information fusion of gas sensitivity and chromatography and on-site detection and analysis of flavor substances using an electronic nose instrument of claim 1, wherein a [1 s, Ts] interval of the gas sampling period T is the chromatographic separation, discharging, cleaning and purging stage of the capillary gas chromatographic column module II for T-1 s; in this stage, setting the two-position three-port electromagnetic valve III-6 to be at "2", whether the other two-position two-port electromagnetic valves are on or off is of little significance at this stage; due to the pushing action of carrier gas $H_2$, separating, the tested odor in the capillary gas chromatographic column II-1, generating, by the detector II-2, a sensitive response, amplifying, through the amplifier II-3, the sensitive response, recording, by the recorder II-4, a sensitive response in an interval of [0, 470 s] or a duration of 470 s, and saving the recorded sensitive response in a temporary file of the computer mainboard IV-3; and not recording the sensitive data in an interval of [T-10 s, T] or a duration of 10 s in the discharging, cleaning and purging stage.

8. The method for multi-information fusion of gas sensitivity and chromatography and on-site detection and analysis of flavor substances using an electronic nose instrument of claim 1, wherein the gas sensor array module I and the capillary gas chromatographic column module II simultaneously enter an information selection and analysis operation region for a last 10 s of the gas sampling period T;

selecting, by the computer control and analysis module IV, 3 pieces of sensitive information from the $i^{th}$ gas sensor in a [1 s, 61 s] headspace sampling time stage of the gas sampling period T, namely, from a voltage response curve having a 60 s duration and recorded in a temporary file simultaneously, to meet a triangular stability principle and thus improve the qualitative and quantitative capability of the gas sensor array, wherein the 3 pieces of sensitive information comprises a steady-state maximum response $v_{gs\_i}(\tau)$, a corresponding peak time value $t_{gs\_i}(\tau)$, and an area $A_{gs\_i}(\tau)$ under the 60 s voltage response curve; obtaining, by the computer control and data analysis module IV, 16*3=48 sensitive variables in total from 16 response curves of the gas sensor array I-1 with 16 gas sensor elements;

selecting, by the computer control and data analysis module IV, 21 sensitive variables from a semi-separated chromatogram of the capillary gas chromatographic column II-1 in an interval of [0, T-10 s] or a duration of T-10 s; where the 21 sensitive variables comprise the first 10 maximum chromatographic peaks $h_{gc\_i}(\tau)$, the 10 corresponding retention time values $t_{gc\_i}(\tau)$, and an area $A_{gc}(\tau)$ under a chromatogram curve; in a case where the number q of chromatographic peaks of the semi-separated chromatogram with a duration of T-10 s is less than 10, selecting, by the computer control and data analysis module IV, the first q<10 maximum chromatographic peaks $h_{gc\_i}(\tau)$, the 10 corresponding retention time values $t_{gc\_i}(\tau)$, and 1 area $A_{gc}(\tau)$ under the chromatogram curve from the semi-separated chromatogram, and performing a zero-padded operation for those not enough chromatographic peaks and retention time values; wherein the obtained chromatographic sensitive information is $X_{gc}(\tau)=\{(h_{gc\_1}(\tau), h_{gc\_2}(\tau), \ldots, h_{gc\_q}(\tau), 0, \ldots, 0); (t_{gc\_1}(\tau), t_{gc2}(\tau), \ldots, t_{gc\_q}(\tau), 0, \ldots, 0); A_{gc}(\tau)\}$; and in the gas sampling period T, fusing, by the computer control and data analysis module IV, through a normalized pre-processing, 48 sensitive variables extracted from the 16 response curves of the gas sensor array I-1 and 21 sensitive variables extracted from the semi-separated chromatogram of the capillary gas chromatographic column II-1 to obtain a sensitive vector $x(\tau) \in R^{69}$ with m=48+21=69 dimensions, saving the sensitive vector $x(\tau) \in R^{69}$ in a specified file of a hard disk of the computer mainboard IV-3; and using as a numerical basis of doing a qualitative and quantitative analysis on foods, condiments, fragrances and flavors, and petroleum waxes by the electronic nose instrument.

9. The method for multi-information fusion of gas sensitivity and chromatography and on-site detection and analysis of flavor substances using an electronic nose instrument of claim 1, wherein the computer control and data analysis module IV employs a modular cascade neural network model to perform (i) identification and (ii) sensory quality indicator score and main component quantitative prediction for the foods, condiments, fragrances and flavors, and petroleum waxes; wherein (i) a first level of the modular cascade neural network model comprises n (n−1)/2 single-output neural networks in parallel to form n vote recognition groups, and the n vote recognition groups are used for identifying n foods, condiments, fragrances and flavors, and petroleum waxes, comprising brands, producing places, authenticity and fragrance types, one for one; (ii) a second level of the modular cascade neural network model comprises n×q single-output neural networks in parallel; q single-output neural networks form one group and are used for quantitatively predicting q indices comprising odor intensity grades and main component concentrations of n foods, condiments, fragrances and flavors, and petroleum waxes;

in a learning stage of the first level (i) of the modular cascade neural network model, making the big odor data, namely a training set X, be done an one-to-one decomposition based on brands, production places, authenticity and odor types to form n(n−1)/2 binary-class training subsets; then, learning the n(n−1)/2 subsets by using n(n−1)/2 single-output neural networks in the first level of the modular cascade neural network model with an error back-propagation algorithm, each for one; making all the single-output neural networks be single-hidden-layer in structure, that is, the number of input nodes is m=69, the number of hidden nodes is $s_1$=8, and the number of output nodes is 1; making the n(n−1)/2 single-output neural networks form n vote recognition groups, and making each single-output neural network takes and only take part into two vote recognition groups among;

in a learning stage of the second level (ii) of the modular cascade neural network model, making the big odor data, namely the training set X, be done the one-to-one decomposition based on brands, production places, authenticity and odor types again, to form n×r single-output regression training subsets; fitting, by n×q single-output neural networks in the second level, to fit the multi-input single-output nonlinear curves for the q indices, each for one, wherein the q indices comprise a sensitive vector $x_p$ of gas sensitivity and gas chromatography, and making all the single-output neural networks be single-hidden-layer in structure, i.e., the number of input nodes is m=69, the number of hidden nodes is $s_2$=5, and the number of output nodes is 1; and identifying, by the modular cascade neural network model, n kinds of foods, condiments, fragrances and flavors, and petroleum waxes by using a majority vote decision-making rule; a decision-making rule for identifying an unknown pattern x is that x belongs to a brand, a production place, a authenticity and a type of the foods, condiments, fragrances and flavors, and petroleum waxes represented by a vote recognition group with the most votes; on the premise that the vote number of a vote recognition group $\Omega_j$ is the max in the first level of the cascade model, and predicting an intensity grade and main component concentration values of x, by a quantitation prediction group $\Lambda_j$ in the second level of the cascade model corresponding to the vote recognition group $\Omega_j$.

10. The method for performing an on-site detection and analysis of flavor substances by using multi-information fusion technology of gas sensitivity and gas chromatography of an electronic nose instrument of any one of claims 1 to 9, wherein performing, by the electronic nose instrument, the real-time on-site detection and prediction of various foods, condiments, fragrances and flavors, and petroleum waxes comprises the following steps:

(1) Power-on: setting a preheating time length of the electronic nose instrument to be 30 min; and setting a "gas sampling period T" value to be a default value T=8 min in the screen menu;

setting the first two-position two-port electromagnetic valve III-4 and the second two-position two-port electromagnetic valve III-5 to be on, setting the fourth two-position two-port electromagnetic valve III-9 to be off, and making the ambient air flow through, at a flow rate of 6,500 ml/min, the side-hole sampling needle III-10, the gas sensor array I-1 inside the annular working chamber I-2, the second two-position two-port electromagnetic valve III-5, the first two-position two-port electromagnetic valve III-4 and the first flowmeter III-2 in order, and finally discharging to outdoor; and making an internal temperature of the annular working chamber I-2 of the gas sensor array reach a constant temperature of 55±0.1° C.;

setting the two-position three-port electromagnetic valve III-6 to be at "2", under the pushing action of the carrier gas $H_2$, making the capillary gas chromatographic column II-1 gradually recover to a reference state, and making the internal temperature in a chromatographic column box reach a constant temperature of 250-300±0.1° C.;

preparation and temperature constant of a tested sample; firstly pipetting by an operator, 10-30 ml tested sample VI-5 into the glass sample bottle VI-6, then placing the glass sample bottle VI-6 into the heat conduction sleeve VI-3 of the large-volume headspace vapor generation device VI, covering with the silicone rubber sealing sheet VI-7, and screwing the cup cover VI-8; pressing an confirmation key to start a constant-temperature time, starting to heat the tested sample VI-5, rising the temperature to 45~80±0.1° C. from the room temperature within 8 min, and accurately keeping the temperature constant for 20~30 min;

(2) starting the gas sampling period T of the $k^{th}$ tested sample VI-5, and taking T=8 min as an example below;

(2.1) the gas sensor array module I:

(2.1a) the headspace sampling stage: in an 1 s-61 s interval of the gas sampling period T, setting the second two-position two-port electromagnetic valve III-5 to be on, setting the first two-position two-port electromagnetic valve III-4, the third two-position two-port electromagnetic valve III-8 and the fourth two-position two-port electromagnetic valve III-9 to be all off, and under the suction action of the first micro vacuum pump III-1, making the headspace vapor of the tested sample VI-5 flow through, at a theoretical flow rate of 1,000 ml/min, the side-hole sampling needle III-10, the annular working chamber I-2 plus the gas sensor array I-1, the second two-position two-port electromagnetic valve III-5, the first throttle valve III-3 and the first flowmeter III-2 in order, and finally, discharging the used headspace vapor to outdoor for 60 s, whereby generating, by the gas sensor array I-1, a sensitive response for the tested odor, and saving a response data in a temporary file of the computer mainboard IV-3 for 60 s, and making the initial 0 s-1 s to be the headspace sampling stage of the capillary gas chromatographic column II;

(2.1b) the transition stage: in a 61 s-65 s interval of the gas sampling period T, setting the second two-position two-port electromagnetic valve III-5 to be on, and setting the first two-position two-port electromagnetic valve III-4, the third two-position two-port electromagnetic valve III-8 and the fourth two-position two-port electromagnetic valve III-9 to be off; making, by the automatic lifter V, the large-volume headspace vapor generation device VI descend by 20 mm within 3 s; keeping the first micro vacuum pump III-1 to suck at a flow rate of 1,000 ml/min, and along with the descending of the large-volume headspace vapor generation device VI, and making the gas flowing inside the annular working chamber I-2 gradually transition to the ambient air from the headspace vapor of the tested sample VI-5;

(2.1c) the rough recovery stage: in a 65 s-435 s interval of the gas sampling period T, setting the first two-position two-port electromagnetic valve III-4 and the second two-position two-port electromagnetic valve III-5 to be on, setting the fourth two-position two-port electromagnetic valve III-9 to be off, and under the suction action of the first micro vacuum pump III-1, making the ambient air flow through, at a flow rate of 6,500 ml/min, the side-hole sampling needle III-10, the gas sensor array I-1 inside the annular working chamber I-2, the second two-position two-port electromagnetic valve III-5, the first two-position two-port electromagnetic valve III-4 and the first flowmeter III-2 in order, and finally discharging the ambient air to outdoor for 370 s, whereby making the gas sensor array I-1 roughly recover to a reference state under the role of the ambient air;

(2.1d) the accurate calibration stage: in a 435 s-475 s interval of the gas sampling period T, setting the fourth two-position two-port electromagnetic valve III-9 to be on, setting the second two-position two-port electromagnetic valve III-5 to be off, and making the dry air in the dry air bottle VII-2 flow through, at a flow rate of 1,000 ml/min, the first pressure reducing valve III-11, the first purifier III-12, the second throttle valve III-13, the fourth two-position two-port electromagnetic valve III-9, the gas sensor array I-1 inside the annular working chamber I-2, the side-hole sampling needle III-10 in order, and finally discharging the dry air to indoor for 40 s, whereby making the gas sensor array I-1 accurately recover to a reference state; in the reference state, placing, by the operator, a tested sample on the support disc V-1 of the automatic lifter V through the large-volume headspace vapor generation device VI in a precise thermostatic process, and preparing next headspace sampling period; and (2.1e) the balance stage, in a 475 s-480 s interval of the gas sampling period T, setting all the two-position two-port electromagnetic valves to be off, and making no gas flow inside the annular working chamber I-2 of the gas sensor array for 5 s; from the 475th second, making, by the automatic lifter V, the large-volume headspace vapor generation device VI up 20 mm within 3 s;

(2.2) the capillary gas chromatographic column II module:

(2.2a) the headspace sampling stage: in a 0 s-1 s interval of the gas sampling period T, setting the two-position three-port electromagnetic valve III-6 to be at "1", setting the third two-position two-port electromagnetic valve III-8 to be on, and setting the second two-position two-port electromagnetic valve III-5 and the fourth two-position two-port electromagnetic valve III-9 to be off; under the suction action of the second micro vacuum pump III-7, making the headspace vapor of the tested sample VI-5 flow through, at a default flow rate of 6 ml/min, the third two-position two-port electromagnetic valve III-8, the two-position three-port electromagnetic valve III-6 and the fourth throttle valve III-18 in order, mixing with the carrier gas $H_2$ at the inlet port II-8 and then flowing into the capillary gas chromatographic column II-1 for 1.0 s, wherein an accumulated sampling volume of the tested headspace vapor is 0.1 ml by default;

(2.2b) the gas chromatographic separation stage: in an [1 s, 480 s] interval of the gas sampling period T, setting the two-position three-port electromagnetic valve III-6 to be at "2", and under the pushing action of the carrier gas $H_2$, separating, the tested headspace vapor, in the 30 m capillary gas chromatographic column II-1; generating, by the detector II-2, a sensitive response, amplifying, by the amplifier II-3, the sensitive response, recording, by the recorder II-4, the sensitive response with a [0, 470 s] interval or a 470 s duration to form a semi-separated chromatogram, and saving the semi-separated chromatogram in the temporary file of the computer mainboard IV-3;

(2.3) the information selection and analysis stage: in a 470 s-480 s interval of the gas sampling period T, selecting, by the computer control and data analysis module IV, 3 pieces of sensitive information, i.e., a steady-state peak value $v_{gs\_i}(\tau)$, a corresponding peak time value $t_{gs\_i}(\tau)$, and an area $A_{gs\_i}(\tau)$ under the curve from the voltage response curve of the $i^{th}$ gas sensor which is recorded in the [1 s, 60 s] time stage; selecting 21 sensitive response variables, i.e., the first 10 max chromatographic peak values $h_{gc\_i}(\tau)$, the 10 corresponding retention time values $t_{gc\_i}(\tau)$, and one area $A_{gc}(\tau)$ under a chromatogram curve from the semi-separated chromatogram which is recorded in a [0 s, 470 s] stage, and saving them in the temporary file of the computer mainboard IV-3; whereby, obtaining, by the computer control and data analysis module IV, one sensitive vector $x(\tau) \in R^{69}$ with 69 dimensions from the sensitive information of the gas sensor array module I and the capillary chromatographic column module II for the tested sample VI-5; then, performing, by the cascade machine learning model, the type identification of a tested odor and the quantitative prediction of its whole intensity as well as main component concentrations s according to the sensitive vector $x(\tau)$, displaying, by the monitor, a detection and prediction result, and then transmitting the result to a central control room and a plurality of fixed/mobile terminals through the Internet; and (3) repeat the step (2), realizing, by the electronic nose instrument, the real-time on-site detection and identification of foods, condiments, fragrances and flavors, and petroleum waxes samples and quantitative prediction of their intensity and main component concentration index values.

* * * * *